US008357367B2

(12) United States Patent
Virca et al.

(10) Patent No.: US 8,357,367 B2
(45) Date of Patent: Jan. 22, 2013

(54) ANTIBODIES THAT BIND PAR-2

(75) Inventors: G. Duke Virca, Bellevue, WA (US); Shaw-Fen Sylvia Hu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 303 days.

(21) Appl. No.: 12/215,304

(22) Filed: Jun. 26, 2008

(65) Prior Publication Data

US 2011/0059063 A1 Mar. 10, 2011

Related U.S. Application Data

(60) Provisional application No. 61/058,094, filed on Jun. 2, 2008, provisional application No. 60/947,264, filed on Jun. 29, 2007.

(51) Int. Cl.
*A61K 39/395* (2006.01)
*C07K 16/00* (2006.01)
(52) U.S. Cl. ............... 424/130.1; 424/141.1; 530/387.1; 530/388.1
(58) Field of Classification Search .................... None
See application file for complete search history.

(56) References Cited

U.S. PATENT DOCUMENTS 5,716,789 A 2/1998 Sundelin et al.
2007/0237759 A1 10/2007 Virca et al.

FOREIGN PATENT DOCUMENTS

WO WO 01/52883 7/2001
WO WO 2004/080373 9/2004
WO WO 2007/092640 A3 8/2007

OTHER PUBLICATIONS

Brown et al., Tolerance of single, but not multiple, amino acid replacements in antibody VH CDR 2: a means of minimizing B cell wastage from somatic hypermutation? J. Immunology 156: 3285-3291, 1996.*
Vajdos et al., Comprehensive functional maps of the antigen-binding site of an anti-ErbB2 antibody obtained with shotgun scanning mutagenesis. J. Mol. Biol. 320:415-428, 2002.*
Rudikoff et al., Single amino acid substitution altering antigen-binding specificity. Proc. Natl. Acad. Sci. USA 79:1979-1983, 1982.*
Paul, William, Fundamental Immunology, 3rd Edition, Raven Press, New York, 1993, pp. 292-295.*
Kelso, E. et al., "Expression and proinflammatory role of proteinase-activated receptor 2 in rheumatoid synovium—Ex vivo studies using a novel proteinase-activated receptor 2 antagonist," *Arthritis & Rheumatism*, 56(3):765-771, 2007.
Mandal, S. et al., "Tissue factor trafficking in fibroblasts: Involvement of protease-activated receptor-mediated cell signaling," Blood, 110(1):161-170, 2007.
Ui et al., "Potent pruritogenic action of tryptase medicated by PAR-2 receptor and its involvement in anti-pruritic effect of nafamostat mesilate in mice," *Eur. J. Pharma.*, 530(1-2):172-178, 2006.
Yoshida, N. et al., "Interleukin-8 production via protease-activated receptor 2 in human esophageal epithelial cells," *Int. J. Mol. Med.*, 19(2):335-340, 2007.
D'Andrea et al., "Characterization of protease-activated receptor-2 immunoreactivity in normal human tissues," *J. Histochem . Cytochem.* 46(2): 157-164, 1998.
Ferrell, et al., "Essential role for proteinase-activated receptor-2 in arthritis," J. Clin. Invest. 111(1): 35-41, 2003.
Kelso et al., "Therapeutic promise of proteinase-activated receptor-2 antagonism in joint inflammation," *J. Pharmacol. Exp. Ther.* 316(3): 1017-1024, 2006.
Koo et al., "Factor Xa induces mitogenesis of coronary artery smooth muscle cell via activation of Par-2," *FEBS Letters 523*: 85-89, 2002.
Maeda et al., "Proinflammatory role of trypsin and protease-activated receptor-2 in a rat model of acute pancreatitis," *Pancreas 31*(1): 54-62, 2005.
McGuire et al., "2-Furoyl-LIGRLO-amide: A potent and selective proteinase-activated receptor 2 agonist," *J Pharmacol Exp. Ther. 309*(3): 1124-1131, 2004.
Molino et al., "Differential expression of functional protease-activated receptor-2 (PAR-2) in human vascular smooth muscle cells," *Arterioscler. Thromb. Vasc. Biol. 18*: 825-832, 1998.
Nystedt et al., "Molecular cloning and functional expression of the gene encoding the human proteinase-activated receptor 2," *Eur. J. Biochem. 232*: 84-89, 1995.
Saifeddine et al., "Rat proteinase-activated receptor-2 (PAR-2): cDNA sequence and activity of receptor-derived peptides in gastric and vascular tissue," *Br. J. of Pharmacology* 118: 521-530, 1996.
Schmidlin, et al., "Protease-activated receptor 2 mediates eosinophil infiltration and hyperactivity in allergic inflammation of the airway," *J. Immunol. 169*: 5315-5321, 2002.
Seeliger et al., "Proinflammatory role of proteinase-activated receptor-2 in humans and mice during cutaneous inflammation in vivo," *FASEB J. 17*: 1871-1885, 2003.
Wang et al., "Up-regulation and activation of proteinase-activated receptor 2 in early and delayed radiation injury in the rat intestine: influence of biological activators of proteinase-activated receptor 2," *Radiat. Res. 160*: 524-535, 2003.
PAR-2 (SAM11) Antibody sc 13504, Santa Cruz Biotechnology, Inc., 2 pages, 2008.
MAB3949, Monoclonal Anti-human *PAR-2* Anitbody, R&D Systems, 2007.
B. Al-Ani and M. D. Hollenberg, "Selective tryptic cleavage at the tethered ligand site of the amino terminal domain of proteinase-activated receptor-2 in intact cells," *J. Pharmacol and Exp Ther.*, 304(3):1120-1128, 2003.
S. Böhm et al., "Molecular cloning, expression and potential functions of the human proteinase-activated receptor-2," *Biochem. J.*, 314:1009-1016, 1996.
M. Fox et al., "Identification of potential activators of proteinase-activated receptor-2," *FEBS Lett*, 417:267-269, 1997.
M. Molino et al., Interactions of mast cell tryptase with thrombin receptors and PAR-2, *J. Biol. Chem.*, 272(7):4043-4049, 1997.

* cited by examiner

Primary Examiner — Ruixiang Li
(74) Attorney, Agent, or Firm — Patricia Anne Perkins

(57) ABSTRACT

The present invention provides compositions and methods relating to or derived from anti-PAR-2 antibodies. In particular embodiments, the invention provides human antibodies that bind PAR-2, PAR-2-binding fragments and derivatives of such antibodies, and PAR-2-binding polypeptides comprising such fragments. Other embodiments provide nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having PAR-2-related disorders or conditions.

5 Claims, 2 Drawing Sheets

ANTIBODIES THAT BIND PAR-2

CROSS REFERENCE TO RELATED APPLICATIONS

This application claims the benefit under 35 U.S.C. §119 of U.S. Provisional Application Ser. No. 61/058,094, filed Jun. 2, 2008 and U.S. Provisional Application Ser. No. 60/947,264, filed Jun. 29, 2007, which are hereby incorporated by reference.

FIELD OF THE INVENTION

This application provides compositions and methods relating to PAR-2 antigen binding proteins.

BACKGROUND OF THE INVENTION

The Proteinase-activated receptor (PAR) family is a part of the seven-transmembrane G-coupled receptor superfamily. There are currently four known PARs, of which three (PARs-1, -3 and -4) are activated by thrombin; a fourth (PAR-2) is activated by trypsin or mast cell tryptase, but not by thrombin. PARs are widely distributed to a variety of tissues and participate in a number of physiological or pathophysiological phenomena such as platelet aggregation, inflammation and cardiovascular, digestive or respiratory functions.

PARs differ from other receptors in that activation is initiated by proteolytic cleavage of the N terminus of the PAR, which then forms a tethered ligand that interacts with the extracellular region (loop 2) of the same receptor polypeptide. Cleavage of PAR-2 occurs between the R and S residues of the protease cleavage domain, SKGRSLIG (amino acids 33 through 40 of SEQ ID NO:2), which is conserved between human, murine and rat PAR-2. Peptides that mimic the tethered ligand have been shown to have agonistic effects on PAR-2 (Saifeddine et al., Br J Pharmacol 118(3):521-30 [1996]; McGuire et al., J Pharmacol Exp Ther 309(3):1124-31 [2004]).

PAR-2 activates the G-protein-coupled receptor-mediated common signal transduction pathways, inositol 1,4,5-trisphosphate production and mobilization of Ca(2+), as well as multiple kinase pathways, including ERK, p38MAPK, JNK, and IKK. It is present on epithelial and endothelial cells, myocytes, fibroblasts, immune cells, neurons and glial cells in the kidney, pancreas, stomach, intestine, airway, skin, bladder and brain. The protease that activates PAR-2 is present during inflammation, and PAR-2 is upregulated by inflammatory factors such as tumour necrosis factor alpha, interleukin 1 alpha and lipopolysaccharide. Moreover, studies utilizing PAR-2-deficient or -overexpressing mice confirm a role for this receptor in inflammation (Schmidlin et al., J. Immunol. 169, 5315-5321 [2002]; Ferrell et al., J. Clin. Invest. 111, 35-41 [2003]). Accordingly, there is a need in the art to develop antagonists of PAR-2 activation, which will be useful in treating or ameliorating inflammatory conditions.

SUMMARY OF THE INVENTION

Figure 1A:
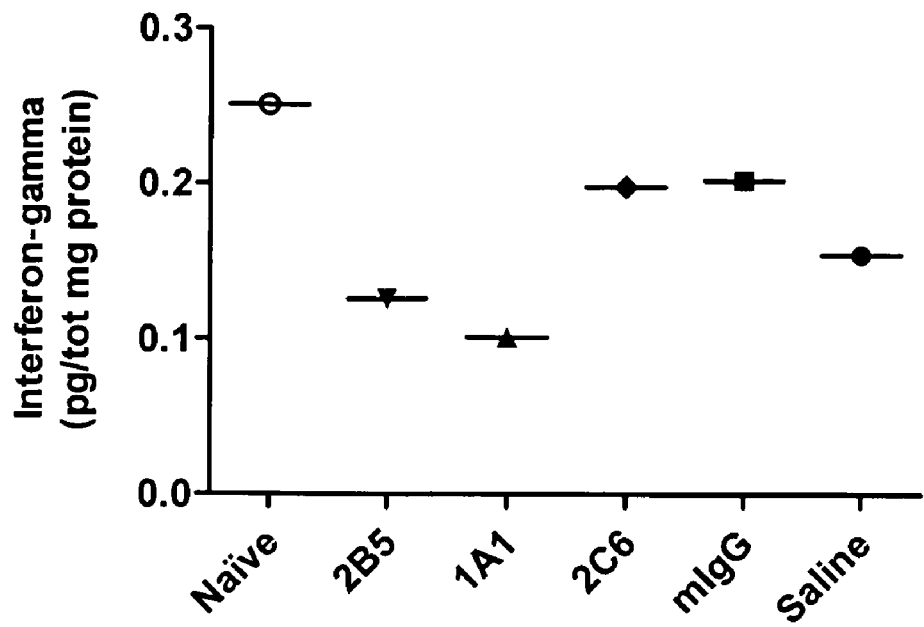
FIG. 1 provides a set of graphs comparing the levels of certain proinflammatory cytokines present in paw tissue from rats in an adjuvant-induece arthritis model.

In one aspect, the present invention provides an isolated antigen binding protein that specifically binds to human PAR-2. In another aspect of the invention, the antigen binding protein specifically binds to the PAR-2 of a non-human primate, a cynomologous monkey, a chimpanzee, a non-primate mammal, a rodent, a mouse, a rat, a hamster, a guinea pig, a cat, or a dog. In another embodiment, the isolated antigen binding protein comprises: a. a human antibody; b. a chimeric antibody; c. a monoclonal antibody; d. a recombinant antibody; e. an antigen-binding antibody fragment; f. a single chain antibody; g. a diabody; h. a triabody; i. a tetrabody; j. a Fab fragment; k. a F(ab')$_2$ fragment; l. a domain antibody; m. an IgD antibody; n. an IgE antibody; o. an IgM antibody; p. an IgG1 antibody; q. an IgG2 antibody; r. an IgG3 antibody; s. an IgG4 antibody; or t. an IgG4 antibody having at least one mutation in a hinge region that alleviates a tendency to form intra-H chain disulfide bond.

In another aspect of the invention, the present invention provides an isolated antigen binding protein having a heavy chain and a light chain, the heavy chain comprising a variable region that is at least 95% identical to SEQ ID NO:9, and the light chain comprising a variable region that is at least 95% identical to SEQ ID NO:11. In another embodiment, the heavy chain variable region is at least 95% identical to SEQ ID NO:31, and the light chain variable region is at least 95% identical to SEQ ID NO:35. In another aspect of the invention, the light chain variable region has the amino acid sequence of SEQ ID NO:39, and the heavy chain variable region has the amino acid sequence of SEQ ID NO:40. In another embodiment of the invention, the light chain variable region has the amino acid sequence of SEQ ID NO:41, and the heavy chain variable region has the amino acid sequence of SEQ ID NO:42.

In one embodiment of the invention, the heavy chain variable region comprises three complementarity determining regions (CDRs) designated CDR1, CDR2 and CDR3, and the light chain variable region comprises three complementarity determining regions (CDRs), designated CDR1, CDR2 and CDR3. In another aspect of the invention, the heavy chain variable region further comprises four framework regions (FRs) designated FR1, FR2, FR3 and FR4, and the light chain variable region further comprises four framework regions (FRs) designated FR1, FR2, FR3 and FR4. In one embodiment of the invention, the heavy chain CDRs are selected from the among CDRs of the peptides having the amino acid sequences shown in SEQ ID NOs:9, 13, 17, 23, 27, 31, and 35, and the light chain CDRs are selected from among the CDRs of the peptides having the amino acid sequences shown in SEQ ID NOs:11, 15, 19, 25, 29, 33 and 37.

In one aspect of the invention, all three heavy chain CDRs are selected from the same peptide, for example, heavy chain CDR1, CDR2 and CDR3 are from SEQ ID NO:9 and light chain CDR1, CDR2 and CDR3 are from SEQ ID NO:11, etc. In another embodiment of the invention, the CDRs are selected from among different peptides, for example, heavy chain CDR1 is from SEQ ID NO:9, CDR2 is from SEQ ID NO:13 and CDR3 from SEQ ID NO:17, and light chain CDR1 is from SEQ ID NO:11, CDR2 is from SEQ ID NO:15 and CDR3 from SEQ ID NO:19, etc. Alternatively, two CDRs can be selected from a single peptide and the third from another peptide. Numerous such combinations are possible. In another aspect the framework regions can be selected from the same peptide, or one or more framework regions can be selected from different peptides.

In one aspect of the invention, the present invention provides nucleic acids encoding the aforementioned polypeptides. In another aspect of the invention the nucleic acid is a vector. In another embodiment of the invention, the invention provides host cells transformed or transfected with the inventive nucleic acids. In another aspect of the invention, there is provided a method of preparing a polypeptide comprising incubating the host cells under conditions promoting expression of the polypeptides and harvesting the polypeptides.

In another aspect, the present invention provides an isolated cell that secretes an antigen binding protein that binds PAR-2. In another embodiment, the cell is a hybridoma. In another embodiment, the present invention provides a method of making an antigen binding protein that binds human PAR-2, comprising incubating said isolated cell under conditions that allow it to express said antigen binding protein.

In one aspect, the present invention provides an isolated antigen binding protein that binds to proteinase activated receptor-2 (PAR-2). In another embodiment, the isolated antigen binding protein, when bound to a human PAR-2, inhibits proteolytic cleavage and/or subsequent signaling through said human PAR-2. In another embodiment, the isolated antigen binding protein inhibits proteolytic activation of PAR-2 by greater than about 80%. In another embodiment, the isolated antigen binding protein binds to uncleaved PAR-2 and binds to a lesser extent to cleaved PAR-2. In another embodiment, the isolated antigen binding protein inhibits proteolytic activation of PAR-2 by less than about 10%. In another embodiment, the isolated antigen binding protein binds to both cleaved and uncleaved PAR-2 substantially equally.

In another aspect, the present invention provides a pharmaceutical composition comprising the antigen binding protein. In one embodiment, the present invention provides a method of treating a condition in a subject comprising administering to said subject said pharmaceutical composition, wherein said condition is treatable by reducing the activity of PAR-2 in said subject. In another embodiment, said subject is a human being. In another embodiment, said condition is an inflammatory condition of the skin, joints, gastrointestinal system and/or airway. In another embodiment, the method further comprises administering to said subject a second treatment. In another embodiment, said second treatment is administered to said subject before and/or simultaneously with and/or after said pharmaceutical composition is administered to said subject. In another embodiment, said second treatment comprises an anti-inflammatory agent. In another embodiment, said second pharmaceutical composition comprises an agent selected from the group consisting of non-steroidal anti-inflammatory drugs, steroids, and immunomodulating agents. In another embodiment, said method comprises administering to said subject a third treatment.

In another aspect, the present invention provides a method of increasing the longevity of a subject comprising administering to said subject said pharmaceutical composition.

In another aspect, the present invention provides a method of decreasing PAR-2 activity in a subject in need thereof comprising administering to said subject said pharmaceutical composition.

In another aspect, the present invention provides a method of decreasing PAR-2 signaling in a subject in need thereof comprising administering to said subject said pharmaceutical composition.

In another aspect, the present invention provides a method of inhibiting the proteolytic activation of PAR-2 in a subject in need thereof comprising administering to said subject said pharmaceutical composition.

DETAILED DESCRIPTION OF THE INVENTION

The present invention provides compositions, kits, and methods relating to molecules that bind to the Proteinase Activated Receptor 2 ("PAR-2"), including molecules that agonize or antagonize PAR-2, such as anti-PAR-2 antibodies, antibody fragments, and antibody derivatives, e.g., antagonistic anti-PAR-2 antibodies, antibody fragments, or antibody derivatives. Also provided are nucleic acids, and derivatives and fragments thereof, comprising a sequence of nucleotides that encodes all or a portion of a polypeptide that binds to PAR-2, e.g., a nucleic acid encoding all or part of an anti-PAR-2 antibody, antibody fragment, or antibody derivative, plasmids and vectors comprising such nucleic acids, and cells or cell lines comprising such nucleic acids and/or vectors and plasmids. The provided methods include, for example, methods of making, identifying, or isolating molecules that bind to PAR-2, such as anti-PAR-2 antibodies, methods of determining whether a molecule binds to PAR-2, methods of determining whether a molecule agonizes or antagonizes PAR-2, methods of making compositions, such as pharmaceutical compositions, comprising a molecule that binds to PAR-2, and methods for administering a molecule that binds PAR-2 to a subject, for example, methods for treating a condition mediated by PAR-2, and for agonizing or antagonizing a biological activity of PAR-2, in vivo or in vitro.

Polynucleotide and polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature without human intervention. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "PAR-2 inhibitor" and "PAR-2 antagonist" are used interchangeably. Each is a molecule that detectably inhibits at least one function of PAR-2. Conversely, a "PAR-2 agonist" is a molecule that detectably increases at least one function of PAR-2. The inhibition caused by a PAR-2 inhibitor need not be complete so long as it is detectable using an assay. Any assay of a function of PAR-2 can be used, examples of which are provided herein. Examples of functions of PAR-2 that can be inhibited by a PAR-2 inhibitor, or increased by a PAR-2 agonist, include protease-activated ligand binding, downstream signaling, and so on. Examples of types of PAR-2 inhibitors and PAR-2 agonists include, but are not limited to, PAR-2 binding polypeptides such as antigen binding proteins (e.g., PAR-2 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts. A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The present invention also provides non-peptide analogs of PAR-2 binding polypeptides. Non-peptide analogs are commonly used in the pharmaceutical industry as drugs with properties analogous to those of the template peptide. These types of non-peptide compound are termed "peptide mimetics" or "peptidomimetics," see, for example, Fauchere, J. Adv. Drug Res. 15:29 (1986); Veber and Freidinger TINS p. 392 (1985); and Evans et al. J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5$^{th}$ Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886, 152 and 5,877,293.

The term "chimeric antibody" refers to an antibody that contains one or more regions from one antibody and one or more regions from one or more other antibodies. In one embodiment, one or more of the CDRs are derived from a human anti-PAR-2 antibody. In another embodiment, all of the CDRs are derived from a human anti-PAR-2 antibody. In another embodiment, the CDRs from more than one human anti-PAR-2 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-PAR-2 antibody, and the CDRs from the heavy chain from a third anti-PAR-2 antibody. Other combinations are possible and are included within the embodiments of the invention.

Further, the framework regions may be derived from one of the same anti-PAR-2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind PAR-2). See, e.g., U.S. Pat. No. 4,816,567 and Morrison, 1985, Science 229:1202-07.

A "neutralizing antibody" or an "inhibitory antibody" is an antibody that inhibits the proteolytic activation of PAR-2 when an excess of the anti-PAR-2 antibody reduces the amount of activation by at least about 20% using an assay such as those described herein in the Examples. In various embodiments, the antigen binding protein reduces the amount of amount of proteolytic activation of PAR-2 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human PAR-2) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions.

Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

PAR-2

As discussed previously, PAR-2 is member of the seven-transmembrane G-coupled receptor superfamily; activation is initiated by proteolytic cleavage of the N terminus to form a tethered ligand. The nucleotide and amino acid sequences of human PAR-2 are shown in SEQ ID NOs:1 and 2; the amino acid sequence of mouse PAR-2 is shown in SEQ ID NO:3 and that of rat PAR-2 is shown in SEQ ID NO:4. Proteolytic cleavage yields the active form of this receptor, which is referred to interchangeably herein as "cleaved" or "clipped" PAR-2.

Antigen Binding Proteins

In one aspect, the present invention provides antigen binding proteins (e.g., antibodies, antibody fragments, antibody derivatives, antibody muteins, and antibody variants) that bind to PAR-2, e.g., human PAR-2.

Antigen binding proteins in accordance with the present invention include antigen binding proteins that inhibit a biological activity of PAR-2. Examples of such biological activities include activation of G-protein-coupled receptor-mediated common signal transduction pathways such as inositol 1,4,5-trisphosphate production and mobilization of Ca(2+), and activation of multiple kinase pathways, including ERK, p38MAPK, JNK, and IKK. Other biological activities include those mediated by PAR-2 in vivo, such as the response to trauma and inflammation; in particular, PAR-2 is involved in the cardiovascular, pulmonary and gastrointestinal systems, where it controls inflammation and nociception (perception of pain). PAR-2 activation also plays a role in the inflammatory response, chronic activation of which can lead to disease conditions.

Different antigen binding proteins may bind to different domains or epitopes of PAR-2 or act by different mechanisms of action. Examples include but are not limited to antigen binding proteins that interfere with proteolytic activation of PAR-2 or that inhibit signal transduction. The site of action may be, for example, intracellular (e.g., by interfering with an intracellular signaling cascade) or extracellular. An antigen binding protein need not completely inhibit PAR-2 induced activity to find use in the present invention; rather, antigen binding proteins that reduce a particular activity of PAR-2 are contemplated for use as well. (Discussions herein of particular mechanisms of action for PAR-2-binding antigen binding proteins in treating particular diseases are illustrative only, and the methods presented herein are not bound thereby.)

Other derivatives of anti-PAR-2 antibodies within the scope of this invention include covalent or aggregative conjugates of anti-PAR-2 antibodies, or fragments thereof, with other proteins or polypeptides, such as by expression of recombinant fusion proteins comprising heterologous polypeptides fused to the N-terminus or C-terminus of an anti-PAR-2 antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG® peptide Asp-Tyr-Lys-Asp-Asp-Asp-Asp-Lys (DYKDDDDK) (SEQ ID NO:7) as described in Hopp et al.,

*Bio/Technology* 6:1204, 1988, and U.S. Pat. No. 5,011,912. The FLAG® peptide is highly antigenic and provides an epitope reversibly bound by a specific monoclonal antibody (mAb), enabling rapid assay and facile purification of expressed recombinant protein. Reagents useful for preparing fusion proteins in which the FLAG® peptide is fused to a given polypeptide are commercially available (Sigma-Aldrich, St. Louis Mo.).

Oligomers that contain one or more antigen binding proteins may be employed as PAR-2 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have PAR-2 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing a PAR-2 binding fragment of an anti-PAR-2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-PAR-2 antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-PAR-2 antibody fragment or derivative fused to a leucine zipper peptide are expressed in suitable host cells, and the soluble oligomeric anti-PAR-2 antibody fragments or derivatives that form are recovered from the culture supernatant.

In one aspect, the present invention provides antigen binding proteins that interfere with the proteolytic activation of a PAR-2. Such antigen binding proteins can be made against PAR-2, or a fragment, variant or derivative thereof, and screened in conventional assays for the ability to interfere with proteolytic activation of PAR-2. Examples of suitable assays are assays that test the antigen binding proteins for the ability to inhibit proteolytic activation of cells expressing PAR-2, or that test antigen binding proteins for the ability to reduce a biological or cellular response that results from the proteolytic activation of cell surface PAR-2 receptors. Additional assays that test the antigen binding proteins include those that qualitatively or quantitatively compare the binding of an antigen binding protein to a full-length, uncleaved PAR-2 polypeptide to the binding of a proteolytically cleaved PAR-2 polypeptide, several examples of which are disclosed herein.

In another embodiment, the present invention provides antigen binding proteins that bind to both cleaved PAR-2 and uncleaved PAR-2. Such antigen binding proteins can be made and screened in conventional assays such as those described above.

In another aspect, the present invention provides an antigen binding protein that demonstrates species selectivity. In one embodiment, the antigen binding protein binds to one or more mammalian PAR-2, for example, to human PAR-2 and one or more of mouse, rat, guinea pig, hamster, gerbil, cat, rabbit, dog, goat, sheep, cow, horse, camel, and non-human primate PAR-2. In another embodiment, the antigen binding protein binds to one or more primate PAR-2, for example, to human PAR-2 and one or more of cynomologous, marmoset, rhesus, and chimpanzee PAR-2. In another embodiment, the antigen binding protein binds specifically to human, cynomologous, marmoset, rhesus, or chimpanzee PAR-2. In another embodiment, the antigen binding protein does not bind to one or more of mouse, rat, guinea pig, hamster, gerbil, cat, rabbit, dog, goat, sheep, cow, horse, camel, and non-human primate PAR-2. In another embodiment, the antigen binding protein does not bind to a New World monkey species such as a marmoset.

In another embodiment, the antigen binding protein does not exhibit specific binding to any naturally occurring protein other than PAR-2. In another embodiment, the antigen binding protein does not exhibit specific binding to any naturally occurring protein other than mammalian PAR-2. In another embodiment, the antigen binding protein does not exhibit specific binding to any naturally occurring protein other than primate PAR-2. In another embodiment, the antigen binding protein does not exhibit specific binding to any naturally occurring protein other than human PAR-2. In another embodiment, the antigen binding protein specifically binds to mouse, rat, cynomolgus monkey, and human PAR-2. In another embodiment, the antigen binding protein specifically binds to mouse, rat, cynomolgus monkey, and human PAR-2 with a similar binding affinity. In another embodiment, the antigen binding protein blocks binding of proteolytic activation of mouse, rat, cynomolgus monkey, and human PAR-2. In another embodiment, the antigen binding protein has a similar $IC_{50}$ against mouse, rat, cynomolgus monkey, and human PAR-2 in a Ca2+ mobilization assay.

One may determine the selectivity of an antigen binding protein for a PAR-2 using methods well known in the art and following the teachings of the specification. For example, one may determine the selectivity using Western blot, FACS, ELISA or RIA.

In another aspect, the present invention provides a PAR-2 binding antigen binding protein (for example, an anti-PAR-2 antibody), that has one or more of the following characteristics: binds to both human and murine PAR-2, inhibits the proteolytic activation of human PAR-2, inhibits the proteolytic activation of murine PAR-2, binds to or near the proteolytic cleavage site of PAR-2, causes relatively little down-regulation of cell-surface expressed PAR-2.

Antigen-binding fragments of antigen binding proteins of the invention may be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. patent application Ser. No. 10/194,975 (published Feb. 27, 2003), U.S. Pat. Nos. 5,869,619, 5,225, 539, 5,821,337, 5,859,205, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with a PAR-2 polypeptide, such that antibodies directed against the PAR-2 polypeptide are generated in the animal. One example of a suitable immunogen is a soluble human PAR-2, such as a polypeptide comprising the proteolytic cleavage site of PAR-2, or other immunogenic fragment PAR-2. Another example of a suitable immunogen is cells expressing high levels of PAR-2, or cell membrane preparations therefrom.

Examples of techniques for production and use of transgenic animals for the production of human or partially human antibodies are described in U.S. Pat. Nos. 5,814,318, 5,569, 825, and 5,545,806, Davis et al., 2003, *Production of human antibodies from transgenic mice* in Lo, ed. Antibody Engineering: Methods and Protocols, Humana Press, N.J.:191-200, Kellermann et al., 2002, Curr Opin Biotechnol. 13:593-97, Russel et al., 2000, Infect Immun. 68:1820-26, Gallo et al., 2000, Eur J. Immun. 30:534-40, Davis et al., 1999, Cancer Metastasis Rev. 18:421-25, Green, 1999, J Immunol Methods. 231:11-23, Jakobovits, 1998, Adv Drug Deliv Rev 31:33-42, Green et al., 1998, J Exp Med. 188:483-95, Jakobovits A, 1998, Exp. Opin. Invest. Drugs. 7:607-14, Tsuda et al., 1997, Genomics 42:413-21, Mendez et al., 1997, Nat. Genet. 15:146-56, Jakobovits, 1994, Curr Biol. 4:761-63, Arbones et al., 1994, Immunity. 1:247-60, Green et al., 1994, Nat. Genet. 7:13-21, Jakobovits et al., 1993, Nature 362:255-58, Jakobovits et al., 1993, Proc Natl Acad Sci USA. 90:2551-55. Chen, J. et al., 1993, Int Immunol 5: 647-656, Choi et al., 1993, Nature Genetics 4: 117-23, Fishwild et al., 1996, Nat Biotechnol 14: 845-51, Harding et al., 1995, Ann NY Acad Sci, Lonberg et al., 1994, Nature 368: 856-59, Lonberg, 1994, *Transgenic Approaches to Human Monoclonal Antibodies* in Handbook of Experimental Pharmacology 113: 49-101, Lonberg et al., 1995, Int Rev Immunol 13: 65-93, Neuberger, 1996, Nat Biotechnol 14: 826, Taylor et al., 1992, Nucleic Acids Research 20: 6287-95, Taylor et al., 1994, Int Immunol 6: 579-91, Tomizuka et al., 1997, Nat Gen 16: 133-43, Tomizuka et al., 2000, Proc Natl Acad Sci USA. 97: 722-27, Tuaillon et al., 1993, Proc Natl Acad Sci USA. 90: 3720-24, and Tuaillon et al., 1994, J Immunol 152: 2912-20. These and other examples are also discussed in U.S. Patent application publication 2007-0098715, published May 3, 2007.

In another aspect, the present invention provides monoclonal antibodies that bind to PAR-2. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-

Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with a PAR-2 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a PAR-2 polypeptide. Such hybridoma cell lines, and anti-PAR-2 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block a PAR-2 induced activity. Examples of such screens are provided in the examples below.

Monoclonal antibodies can also be produced using a process referred to as genetic immunization. For example, a nucleic acid encoding the antigen of interest can be incorporated into a viral vector (such as an adenoviral vector). The resulting vector is then used to develop an immune response against the antigen of interest in a suitable host animal (for example, a non-obese diabetic, or NOD, mouse). This techniques is substantially described by Ritter et al., Biodrugs 16(1): 3-10 (2002), the disclosure of which is incorporated by reference herein.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to PAR-2.

Antigen binding proteins directed against a PAR-2 can be used, for example, in assays to detect the presence of PAR-2 polypeptides, either in vitro or in vivo. The antigen binding proteins also may be employed in purifying PAR-2 proteins by immunoaffinity chromatography. Those antigen binding proteins that additionally can block proteolytic activation of PAR-2 may be used to inhibit a biological activity that results from such binding. Blocking antigen binding proteins can be used in the methods of the present invention. Such antigen binding proteins that function as PAR-2 antagonists may be employed in treating any PAR-2-induced condition, including but not limited to inflammatory conditions. In one embodiment, a human anti-PAR-2 monoclonal antibody generated by procedures involving immunization of transgenic mice is employed in treating such conditions.

Antigen binding proteins may be employed in an in vitro procedure, or administered in vivo to inhibit a PAR-2-induced biological activity. Disorders caused or exacerbated (directly or indirectly) by the proteolytic activation of PAR-2, examples of which are provided herein, thus may be treated. In one embodiment, the present invention provides a therapeutic method comprising in vivo administration of a PAR-2 blocking antigen binding protein to a mammal in need thereof in an amount effective for reducing a PAR-2-induced biological activity.

Antigen binding proteins of the invention include partially human and fully human monoclonal antibodies that inhibit a biological activity of PAR-2. One embodiment is directed to a human monoclonal antibody that at least partially blocks proteolytic activation of human PAR-2. In one embodiment, the antibodies are generated by immunizing a transgenic mouse with a PAR-2 immunogen. In another embodiment, the immunogen is a human PAR-2 polypeptide (e.g., a soluble fragment comprising all or part of the PAR-2 cleavage site). Hybridoma cell lines derived from such immunized mice, wherein the hybridoma secretes a monoclonal antibody that binds PAR-2, also are provided herein.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble PAR-2 polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of PAR-2 bound thereto. Polypeptides contemplated for use herein include substantially homogeneous recombinant mammalian anti-PAR-2 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-PAR-2 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-PAR-2 antibody of the invention. Such fragments can consist entirely of antibody-derived sequences or can comprise additional sequences. Examples of antigen-binding fragments include Fab, F(ab')$_2$, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16. Moreover, if an IgG4 is desired, it may also be desired to introduce a point mutation (CPSCP->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antigen binding proteins having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

In particular embodiments, antigen binding proteins of the present invention have a binding affinity ($K_a$) for PAR-2 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present invention provides an antigen binding protein that has a low dissociation rate from PAR-2. In one embodiment, the antigen binding protein has a $K_{off}$ of $1 \times 10^{-4}$ s$^{-1}$ or lower. In another embodiment, the $K_{off}$ is $5 \times 10^{-5}$ s$^{-1}$ or lower. In another embodiment, the $K_{off}$ is substantially the same as an antibody described herein in the Examples. In another embodiment, the antigen binding protein binds to PAR-2 with substantially the same $K_{off}$ as an antibody described herein in the Examples.

In another aspect, the present invention provides an antigen binding protein that inhibits an activity of PAR-2, for example Ca2+ mobilization. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of PAR-2 with substantially the same IC$_{50}$ as an antibody described herein in the Examples.

In another embodiment, the present invention provides an antigen binding protein that binds to full-length PAR-2 and binds to a lesser extent to cleaved PAR-2. In various embodiments, the antigen binding protein binds to full-length PAR-2 by at least 30%, 40%, 50%, 60%, 70%, 75%, 80%, 85%, 90%, 95%, 97%, 99%, and 99.9% more than it binds to cleaved PAR-2.

In another aspect, the present invention provides an antigen binding protein that binds at or near the protease cleavage site of human PAR-2. In one embodiment, an antigen binding protein binds downstream of the cleavage site (i.e., binds both full length and truncated amino-terminal PAR-2-Fc; in another embodiment, whereas an antigen binding protein binds upstream of the cleavage site (i.e., binds only the full-length PAR-2/Fc). Antigen binding proteins that bind to the protease cleavage site can be made using any technique known in the art. For example, such antigen binding proteins can be isolated using the full-length PAR-2 polypeptide (e.g., in a membrane-bound preparation), a soluble extracellular domain fragment of PAR-2, or a smaller fragment of the PAR-2 extracellular domain comprising or consisting of the protease cleavage site (examples of which are provided herein). Antigen binding proteins so isolated can be screened to determine their binding specificity using any method known in the art (examples of which are provided herein).

In another embodiment, the present invention provides an antigen binding protein that competes for binding to PAR-2 with an antibody disclosed herein. Such competitive ability can be determined by methods that are well-known in the art, for example by competition in binding to PAR-2/Fc in a Western blot (or another peptide-based assay), or by competition in a Ca2+ flux assay as described herein. In one aspect, an antigen binding protein that competes for binding to PAR-2 with an antibody disclosed herein binds the same epitope as the antibody. In another aspect, the antigen binding protein that competes for binding to PAR-2 with an antibody disclosed herein inhibits proteolytic activation of PAR-2.

In another aspect, the present invention provides an antigen binding protein that binds to human PAR-2 expressed on the surface of a cell and, when so bound, inhibits PAR-2 signaling activity in the cell without causing a significant reduction in the amount of PAR-2 on the surface of the cell. Any method for determining or estimating the amount of PAR-2 on the surface and/or in the interior of the cell can be used. In one embodiment, the present invention provides an antigen binding protein that binds to or near the protease cleavage site of a human PAR-2 expressed on the surface of a cell and, when so bound, inhibits PAR-2 signaling activity in the cell without significantly increasing the rate of internalization of the PAR-2 from the surface of the cell. In other embodiments, binding of the antigen binding protein to the PAR-2-expressing cell causes less than about 75%, 50%, 40%, 30%, 20%, 15%, 10%, 5%, 1%, or 0.1% of the cell-surface PAR-2 to be internalized.

In another aspect, the present invention provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO 00/09560, published Feb. 24, 2000, incorporated by reference.

The present invention further provides multi-specific antigen binding proteins, for example, bispecific antigen binding protein, e.g., antigen binding protein that bind to two different epitopes of PAR-2, or to an epitope of PAR-2 and an epitope of another molecule, via two different antigen binding sites or regions. Moreover, bispecific antigen binding protein as disclosed herein can comprise a PAR-2 binding site from one of the herein-described antibodies and a second PAR-2 binding region from another of the herein-described antibodies, including those described herein by reference to other publications. Alternatively, a bispecific antigen binding protein may comprise an antigen binding site from one of the herein described antibodies and a second antigen binding site from another PAR-2 antibody that is known in the art, or from an antibody that is prepared by known methods or the methods described herein.

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. Nos. 4,474,893, 6,106,833), and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in Kortt et al., 1997, supra; U.S. Pat. Nos. 5,959,083; and 5,807,706.

In another aspect, the antigen binding protein of the present invention comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. US Pat. App. No. 20030195154.

In another aspect, the present invention provides methods of screening for a molecule that binds to PAR-2 using the antigen binding proteins of the present invention. Any suitable screening technique can be used. In one embodiment, a PAR-2 molecule, or a fragment thereof to which an antigen binding protein of the present invention binds, is contacted with the antigen binding protein of the invention and with another molecule, wherein the other molecule binds to PAR-2 if it reduces the binding of the antigen binding protein to PAR-2. Binding of the antigen binding protein can be detected using any suitable method, e.g., an ELISA. Detection of binding of the antigen binding protein to PAR-2 can be simplified by detectably labeling the antigen binding protein, as discussed above. In another embodiment, the PAR-2-binding molecule is further analyzed to determine whether it inhibits PAR-2 activation and/or signaling.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with PAR-2. The nucleic acid may be isolated by conventional procedures such as polymerase chain reaction (PCR).

The invention further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to PAR-2 or blocking the proteolytic activation of PAR-2).

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence, or a desired fragment, variant, or derivative thereof, is mutated such that it encodes an amino acid sequence comprising one or more deletions or substitutions of amino acid residues. In another embodiment, the mutagenesis inserts an amino acid adjacent to one or more amino acid residues. Alternatively, one or more mutations can be introduced into a nucleic acid that selectively change the biological activity (e.g., binding of PAR-2, inhibiting proteolytic activation of PAR-2, etc.) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a PAR-2 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Indications

In one aspect, the present invention provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of PAR-2. In some such conditions, the expression or activity level is too high, and the treatment comprises administering a PAR-2 antagonist as described herein.

Specific medical conditions and diseases that are treatable or preventable with the antigen binding proteins of this invention include inflammatory conditions of the gastrointestinal system, including coeliac disease, Crohn's disease; ulcerative colitis; idiopathic gastroparesis; pancreatitis, including chronic pancreatitis; inflammatory bowel disease and ulcers, including gastric and duodenal ulcers. The antigen binding proteins of this invention are also useful in treating or ameliorating inflammatory conditions of the airway, such as asthma (including extrinsic and intrinsic asthma as well as related chronic inflammatory conditions, or hyperresponsiveness, of the airways), chronic obstructive pulmonary disease (COPD. i.e., chronic bronchitis, emphysema), Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, occupational asthma, asthma-like disorders, sarcoid, reactive airway disease (or dysfunction) syndrome, byssinosis, interstitial lung disease, hyper-eosinophilic syndrome, rhinitis, sinusitis, and parasitic lung disease, airway hyperresponsiveness associated with viral-induced conditions (for example, respiratory syncytial virus (RSV), parainfluenza virus (PIV), rhinovirus (RV) and adenovirus).

Rheumatic disorders that are treatable with the antigen binding proteins of this invention include adult and juvenile rheumatoid arthritis; scleroderma; systemic lupus erythematosus; lupus-like syndromes; undifferentiated connective tissue disease; gout; osteoarthritis; polymyalgia rheumatica; seronegative spondylarthropathies, including ankylosing spondylitis, and Reiter's disease, psoriatic arthritis and chronic Lyme arthritis. Also treatable or preventable with these polypeptides are Still's disease and uveitis associated with rheumatoid arthritis. In addition, the polypeptide therapies of the invention are used in treating disorders resulting in inflammation of the voluntary muscle and other muscles, including dermatomyositis, inclusion body myositis, polymyositis, and lymphangioleimyomatosis. Additional disorders are also treatable with the present invention, including Guillain-Barre disease, Type I diabetes mellitus, Graves' disease, Addison's disease, Raynaud's phenomenon (including Raynaud's disease and Raynaud's syndrome), autoimmune hepatitis, GVHD (graft versus host disease), and the like.

The disorders described herein can be treated with the antigen binding proteins of this invention in combination with other cytokines, cytokine inhibitors and reagents (also referred to herein as immunomodulators). For example, immunomodulators include IL-18 antagonists such as soluble IL-18 receptor, antibodies to IL-18 or the IL-18 receptor, IL-18 binding protein; TNF inhibitors, including ENBREL®; IL-1 inhibitors, including soluble forms of type I IL-1R, type II IL-1R, antibodies to IL-1, antibodies to type I IL-1R; and or other active agents that are effective in treating the disclosed medical conditions and diseases.

The compositions and/or methods of the present invention also can be used, for example, in cosmetic treatments, in veterinary treatments, to increase longevity, to treat reproductive defects, and to treat a variety of PAR-2 related disorders. In addition, in certain such conditions, the expression or activity level of PAR-2 is too low, and the treatment comprises administering a PAR-2 agonist; such treatments are also comprehended herein.

Therapeutic Methods and Administration of Antigen Binding Proteins

Certain methods provided herein comprise administering a PAR-2 binding antigen binding protein to a subject, thereby reducing a PAR-2-induced biological response that plays a role in a particular condition. In particular embodiments, methods of the invention involve contacting endogenous PAR-2 with a PAR-2 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a PAR-2 antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds PAR-2 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to a PAR-2 binding antigen binding protein In one embodiment, the pharmaceutical composition comprise an antigen binding protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

Kits for use by medical practitioners include a PAR-2-inhibiting substance of the invention and a label or other instructions for use in treating any of the conditions discussed herein. In one embodiment, the kit includes a sterile preparation of one or more PAR-2 binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A PAR-2 inhibiting substance of the invention may be administered, for example, once or more than once, e.g., at regular intervals over a period of time. In particular embodiments, an antigen binding protein is administered over a period of at least a month and more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

Particular embodiments of the present invention involve administering an antigen binding protein at a dosage of from about 1 ng of antigen binding protein per kg of subject's weight per day ("1 ng/kg/day") to about 10 mg/kg/day, more preferably from about 500 ng/kg/day to about 5 mg/kg/day, and most preferably from about 5 µg/kg/day to about 2 mg/kg/day, to a subject. In additional embodiments, an antigen binding protein is administered to adults one time per week, two times per week, or three or more times per week, to treat a PAR-2 mediated disease, condition or disorder, e.g., a medical disorder disclosed herein. If injected, the effective amount of antigen binding protein per adult dose may range from 1-20 $mg/m^2$, and preferably is about 5-12 $mg/m^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of antigen binding protein to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antigen binding protein administered two or three times per week.

Particular embodiments of the methods provided herein involve subcutaneous injection of from 0.5 mg to 10 mg, preferably from 3 to 5 mg, of an antigen binding protein, once or twice per week. Another embodiment is directed to pulmonary administration (e.g., by nebulizer) of 3 or more mg of antigen binding protein once a week.

Examples of therapeutic regimens provided herein comprise subcutaneous injection of an antigen binding protein once a week, at a dose of 1.5 to 3 mg, to treat a condition in which PAR-2 signaling plays a role. Examples of such conditions are provided herein and include, for example, rheumatic conditions as previously described, and other conditions in which excessive inflammation plays a role (described herein; for example, inflammatory bowel disease, pancreatitis, etc). Weekly administration of antigen binding protein is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of a PAR-2 inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an antigen binding protein is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

Elevated levels of PAR-2 and/or activation of PAR-2 are associated with a number of disorders, including, for example, inflammatory conditions of the skin, joints, gastrointestinal system and/or airway. Subjects with a given disorder may be screened, to identify those individuals who have elevated PAR-2 activation, thereby identifying the subjects who may benefit most from treatment with a PAR-2 binding antigen binding protein. Thus, treatment methods provided herein optionally comprise a first step of measuring a subject's PAR-2 activation levels. An antigen binding protein may be administered to a subject in whom PAR-2 activation is elevated above normal.

A subject's levels of PAR-2 activity may be monitored before, during and/or after treatment with an antigen binding protein, to detect changes, if any, in PAR-2 activity. For some disorders, the incidence of elevated PAR-2 activity may vary according to such factors as the stage of the disease or the particular form of the disease. Known techniques may be employed for measuring PAR-2 activity, e.g., in a subject's serum, blood or tissue samples. PAR-2 activity may be measured using any suitable technique.

Particular embodiments of methods and compositions of the invention involve the use of an antigen binding protein and one or more additional PAR-2 antagonists, for example, two or more antigen binding proteins of the invention, or an antigen binding protein of the invention and one or more other PAR-2 antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

Examples of other agents that may be co-administered with an antigen binding protein are other antigen binding proteins or therapeutic polypeptides that are chosen according to the particular condition to be treated. Alternatively, non-proteinaceous drugs that are useful in treating one of the particular conditions discussed above may be co-administered with a PAR-2 antagonist.

Combination Therapy

In another aspect, the present invention provides a method of treating a subject with a PAR-2 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the PAR-2 agonists or antagonists described herein. In another embodiment, the method comprises administering to the subject two or more treatments that together inhibit or activate (directly or indirectly) PAR-2-mediated signal transduction. Examples of such methods include using combinations of two or more PAR-2 inhibiting antigen binding proteins, of a PAR-2 inhibiting antigen binding protein and one or more other therapeutic moiety having anti-inflammatory properties (for example, non-steroidal anti-inflammatory agents, steroids, and/or immunomodulators), or of a PAR-2 inhibiting antigen binding protein and one or more other treatments (e.g., surgery, ultrasound, or treatment effective to reduce inflammation). Furthermore, one or more anti-PAR-2 antibodies or antibody derivatives can be used in combination with one or more molecules or other treatments, wherein the other molecule(s) and/or treatment(s) do not directly bind to or affect PAR-2, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the PAR-2 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

The following examples, both actual and prophetic, are provided for the purpose of illustrating specific embodiments or features of the instant invention and do not limit its scope.

EXAMPLE 1

Preparation of Monoclonal Antibodies

Immunizations are conducted using one or more suitable forms of PAR-2 antigen, including soluble PAR-2 peptide (a loop 1 peptide of PAR-2 [TNRSSKGRSLIGKVDGTS; amino acids 29 through 46 of SEQ ID NO:2], having an additional C-terminal cysteine residue to facilitate conjugation, conjugated to maleiimide-activated keyhole limpet hemocyanin [KLH; obtainable for example from Pierce Biotechnology Inc., Rockford, Ill.]), a PAR-2/Fc fusion protein, and cell-bound PAR-2 (for example, CHO transfectants expressing human PAR-2 at the cell surface, obtainable by transfecting CHO cells with human full length PAR-2 cDNA encoding a polypeptide of SEQ ID NO:2), or combinations thereof.

A suitable amount of immunogen (i.e., ten micrograms/mouse of soluble PAR-2 or $3 \times 10^6$ cells/mouse of transfected CHO cells) are used for initial immunization in XenoMouse™ according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. Following the initial immunization, subsequent boost immunizations of immunogen (five μg/mouse of soluble PAR-2 or $1.5 \times 10^6$ PAR-2 transfected cells/mouse) are administered on a schedule and for the duration necessary to induce a suitable titer of anti-PAR-2 antibody in the mice. Titers are determined by any suitable method, for example, enzyme immunoassay or fluorescence activated cell sorting, or by other methods (including combinations thereof).

Animals exhibiting suitable titers are identified, and lymphocytes are obtained from draining lymph nodes and, if necessary, pooled for each cohort. Lymphocytes may be dissociated from lymphoid tissue by grinding in a suitable medium (for example, Dulbecco's Modified Eagle Medium; DMEM; obtainable from Invitrogen, Carlsbad, Calif.) to release the cells from the tissues, and suspended in DMEM. B cells may be selected and/or expanded using a suitable method, and fused with suitable fusion partner, for example, nonsecretory myeloma P3X63Ag8.653 cells (American Type Culture Collection CRL 1580; Kearney et al, *J. Immunol.* 123, 1979, 1548-1550), using techniques that are known in the art.

In one suitable fusion method, lymphocytes are mixed with fusion partner cells at a ratio of 1:4. The cell mixture is gently pelleted by centrifugation at 400×g for 4 minutes, the supernatant decanted, and the cell mixture gently mixed (for example, by using a 1 ml pipette). Fusion is induced with PEG/DMSO (polyethylene glycol/dimethyl sulfoxide; obtainable from Sigma-Aldrich, St. Louis Mo.; 1 ml per million of lymphocytes). PEG/DMSO is slowly added with gentle agitation over one minute followed, by one minute of mixing. IDMEM (DMEM without glutamine; 2 ml per million of B cells), is then added over 2 minutes with gentle agitation, followed by additional IDMEM (8 ml per million B-cells) which is added over 3 minutes.

The fused cells are gently pelleted (400×g 6 minutes) and resuspended in 20 ml Selection media (for example, DMEM containing Azaserine and Hypoxanthine [HA] and other supplemental materials as necessary) per million B-cells. Cells are incubated for 20-30 minutes at 37 C and then resuspended in 200 ml Selection media and cultured for three to four days in T175 flasks prior to 96 well plating.

Cells are distributed into 96-well plates using standard techniques to maximize clonality of the resulting colonies. After several days of culture, supernatants are collected and subjected to screening assays as detailed in the examples below, including confirmation of binding to human PAR-2, evaluation of cross-reactivity with other species PAR-2 (for example, cynomologous monkey and/or murine PAR-2), binding to cleaved versus uncleaved PAR-2, and ability to inhibit proteolytic activation of PAR-2. Positive cells are further selected and subjected to standard cloning and subcloning techniques. Clonal lines may be expanded in vitro or in vivo, and the secreted human antibodies obtained for analysis.

Hybridoma clones thus generated are screened for reactivity with PAR-2. Initial screening of hybridoma supernatants may utilize a peptide ELISA, a whole cell ELISA and/or a cell-based assay suitable for high-throughput screening (fluorometric microvolume assay technology or FMAT, substantially as described by Fiscella, et al., *Nature Biotechnology* 21:302-307; 2003). Hybridomas that are positive in this screening method may be further cultured to provide larger amounts of antibody, which can then be purified as described below and screened by additional cell-based assay(s) (for example, a flash plate assay using cells co-expressing apoaequorin, a Ca2+-sensitive photoprotein, substantially as described by Le Poul et al., *J. Biomol. Screen.* 7(1):57-65; 2002, and PAR-2), or a fluorometric imaging plate reader (FLIPR) assay, which is used to determine changes in intracellular Ca2+ levels, substantially as described in S. Pitchford, *Genetic Engineering News* vol. 18, Number 15 (1998) and/or Sullivan et al., *Methods in Molecular Biology* vol. 114, pp 125-133 (1999), which are incorporated by reference herein.

In this manner, mice were immunized with either soluble PAR-2, PAR-2 expressing cells or PAR-2/Fc protein, for a total of 19 or 20 immunizations over a period of approximately two-two and one-half months; several cell lines secreting PAR-2-specific antibodies were obtained, and the antibodies further characterized. The sequences thereof are presented in the Sequence Listing and summarized in Table 1 below, and results of various tests using these antibodies are shown herein. Those of skill in the art recognize that the boundaries between framework and complementarity determining regions can vary; for example, amino acid 22 of a light chain FR1 may be considered a part of CDR1 in some instances, etc. Moreover, some numbering systems designate CDR3 and FR4 of a heavy chain as a J region, and may include a D region between FR3 and CDR3. Accordingly, the numbering of the regions set forth below may vary by from one to five amino acids.

TABLE I

|  | VR | FR1 | CDR1 | FR2 | CDR2 | FR3 | CDR3 | FR4 |
| --- | --- | --- | --- | --- | --- | --- | --- | --- |
| 1A1, heavy, SEQ ID NO: 9 | 1-126 | 1-30 | 31-35 | 36-49 | 50-66 | 67-98 | 99-115 | 116-126 |
| 1A1 light, SEQ ID NO: 11 | 1-107 | 1-22 | 23-33 | 34-48 | 49-55 | 56-87 | 88-97 | 98-107 |
| 1B5, heavy, SEQ ID NO: 13 | 1-126 | 1-30 | 31-35 | 36-49 | 50-66 | 67-98 | 99-115 | 116-126 |
| 1B5 light, SEQ ID NO: 15 | 1-107 | 1-22 | 23-33 | 34-48 | 49-55 | 56-87 | 88-97 | 98-107 |

TABLE I-continued

| | VR | FR1 | CDR1 | FR2 | CDR2 | FR3 | CDR3 | FR4 |
|---|---|---|---|---|---|---|---|---|
| 1C7, heavy, SEQ ID NO: 17 | 1-126 | 1-30 | 31-35 | 36-49 | 50-66 | 67-98 | 99-115 | 116-126 |
| 1C7 light, SEQ ID NO: 19 | 1-107 | 1-22 | 23-33 | 34-48 | 49-55 | 56-87 | 88-97 | 98-107 |
| 2A5, light, SEQ ID NO: 21 | 1-106 | 1-22 | 23-33 | 34-48 | 49-55 | 56-87 | 88-96 | 97-106 |
| 2C6, heavy, SEQ ID NO: 23 | 1-122 | 1-30 | 31-35 | 36-49 | 50-66 | 67-98 | 99-110 | 111-122 |
| 2C6, light, SEQ ID NO: 25 | 1-111 | 1-22 | 23-35 | 35-50 | 51-57 | 58-89 | 90-100 | 101-111 |
| 9B12, heavy, SEQ ID NO: 27 | 1-121 | 1-30 | 31-35 | 36-49 | 50-66 | 67-98 | 99-110 | 111-121 |
| 9B12, light, SEQ ID NO: 29 | 1-111 | 1-22 | 23-35 | 36-50 | 51-57 | 58-89 | 90-101 | 102-111 |
| 12D5, heavy, SEQ ID NO: 31 | 1-125 | 1-30 | 31-37 | 38-51 | 52-69 | 70-101 | 102-114 | 115-125 |
| 12D5, light, SEQ ID NO: 33 | 1-107 | 1-23 | 24-34 | 35-49 | 50-56 | 57-88 | 89-97 | 98-107 |
| 13F2, heavy, SEQ ID NO: 35 | 1-125 | 1-30 | 31-37 | 38-51 | 52-69 | 70-101 | 102-114 | 115-125 |
| 13F2, light, SEQ ID NO: 37 | 1-107 | 1-23 | 24-34 | 35-49 | 50-56 | 57-88 | 89-97 | 98-107 |

EXAMPLE 2

Purification of anti-PAR2 Hybridoma Antibodies for Screening

Hybridoma cells are cultured for a time and under conditions to yield a sample of about 35 ml of hybridoma supernatant fluid. Monoclonal antibodies are purified using a suitable method, for example, using protein A. To each sample is added 12 ml of 4×-Protein A Binding Buffer (1.6 M citric acid, 100 mM tris, pH 9.15) and about 300 μl of a 67% slurry of MabSelect™ Media (GE Healthcare, Piscataway, N.J.). The resulting slurry is rotated gently over night at 4° C.

After overnight incubation, the samples are centrifuged to sediment the resin and the monoclonal antibodies bound thereto, for example at 2,000 RPM in a G3.8 centrifuge rotor (Beckman Coulter, Fullerton, Calif.) for 5 minutes at 4° C. with no brake. All but about 300 μl of the supernatant fluid is removed and the resin is resuspended to form a concentrated slurry.

The concentrated slurry is transferred to a microcentrifuge tube and sufficient 1×-Protein A Binding Buffer (400 mM citric acid, 25 mM tris, pH 8.9) is added to bring the total volume up to about 1 ml. The slurry is resuspended, then centrifuged at about 14,000 g for 5 seconds. The supernatant fluid is removed from the resulting pellet, which is washed a total of three times in a similar manner (i.e. by resuspending in about 1 ml of 1×-Protein A Binding Buffer, centrifuging, removing supernatant and resuspending in fresh buffer).

After three washes, the pellet is resuspended in 400 μl Elution Buffer (200 mM formic acid) and agitated for 10 min at room temperature, then centrifuged at 14,000 g for 5 seconds. The supernatant is carefully removed as eluate, and the pellet is eluted again in a manner similar to that described above for a total of three elution cycles. The eluates from the three elution cycles are combined, centrifuged at 14,000 g for 5 min room temperature and transferred to a fresh tube. The pH is adjusted to 7.8-8.2 by adding 2 M tris base (235 mM$_f$) and mixing quickly. The samples are again centrifuged at 14,000 g for 5 min at room temperature, and designated as pH Shift Soluble. A spectral scan of each sample (diluted by adding 20 μl of the sample to 700 μl water) is run from 250 to 350 nm, and protein concentration is verified by loading 0.5 μg each antibody-containing sample on a reducing 4-20% SDS-PAGE gel with an appropriate antibody standard.

EXAMPLE 3

Purification of PAR-2/Fc Polypeptide

N-terminal PAR-2/Fc polypeptide (SEQ ID NO:6) is expressed in suitable mammalian cells such as CHO cells. Expression supernatant from CHO expression cells cultured in serum-free media contain a CHO cell trypsin-like serine protease that cleaves PAR-2/Fc at the activation Arg-Ser bond, generating the "clipped" version of the PAR-2/Fc polypeptide. CHO expression cells cultured in 10% fetal calf serum (which contains normal levels of plasma proteinase inhibitors at concentrations far in excess of the concentration of the CHO cell trypsin-like serine protease) express uncleaved N-terminal PAR-2/Fc in culture supernatants. Both clipped and uncleaved proteins are purified using methods that are suitable for isolation and purification of proteins comprising an Fc regions (for example, using a MabSelect™ resin systems, from GE Healthcare, Piscataway, N.J.)). The resultant purified Fc-constructs are analyzed by amino terminal sequence analysis (Edman degradation), size exclusion chromatrography, absorbance spectral scan, and mass spectroscopy, as needed.

In one example of a suitable purification system, conditioned media containing PAR-2/Fc is loaded on to a GE Healthcare 10 ml Protein A Sepharose™ HiTrap column at 6 ml/min and 7° C. The column is washed with several column volumes of Dulbecco's phosphate buffered saline without divalent cations and then eluted with 100 mM glycine at pH 3.0. The eluted protein is diluted into a Tris buffer and the pH is adjusted 7.0 with 1 M H$_3$PO$_4$. The eluate is then loaded on to a 5 ml GE Healthcare SP-HP HiTrap column in S-Buffer A (20 mM NaH$_2$PO$_4$ at pH 7.0) at 5 ml/min and 7° C. The column is washed with several column volumes of S-Buffer A followed by elution with a 20 column volume linear gradient to 40% S-Buffer B (20 mM NaH$_2$PO$_4$, 1 M NaCl, pH 7.0) followed by a step to 100% S-Buffer B at 5 ml/min and 7° C. The fractions may be analyzed by Coomassie stained SDS-PAGE and pooled. The pooled fractions may be filtered through a 0.22 μm cellulose acetate filter; and a spectral scan can be conducted on a sample, using a calculated molecular mass of 30,226 and a calculated extinction coefficient of 35,410 $M^{-1}$ $cm^{-1}$. The pooled material is concentrated (for example, by using a Pall Macrosep® 10 kDa membrane at room temperature followed by filtration though a 0.22 μm cellulose acetate filter); another spectral scan may be conducted to verify concentration. The final product may then be analyzed by Coomassie stained SDS-PAGE (4-20% 1.0 mm tris-glycine gel) and SE-HPLC using a Phenomenx BioSep 3000 column (7.8×300 mm) in 50 mM NaH2PO4, 250 mM NaCl, pH 6.9.

EXAMPLE 4

Expression and Purification of PAR-2/Fc:FLAG®/Fc Heterodimer

A heterodimeric PAR-2/Fc:FLAG®/Fc protein is expressed and purified to facilitate analysis of the avidity and affinity of antibodies to PAR-2. Suitable cells, for example mammalian cells or human cells such as HEK293 cells, are co-transfected with nucleic acid encoding PAR-2/Fc (SEQ ID NO:5) and nucleic acid encoding FLAG®/Fc (SEQ ID NO:43). Culture of the transfected cells under appropriate conditions (for example in medium containing low-IgG serum) results in expression of homodimeric PAR-2/Fc, homodimeric FLAG®/Fc and heterodimeric PAR-2/Fc:FLAG®/Fc protein. The latter is obtained by sequential purification steps, substantially as described below.

In one example of a suitable purification system, conditioned media containing PAR-2/Fc:FLAG®/Fc is subjected to purification methods that facilitate purification of Fc proteins, similarly to methods described previously for PAR-2/Fc. Briefly, conditioned media is loaded on to a protein A column under conditions that allow the Fc to bind the Protein A. The column is washed with several column volumes of PBS and then eluted at low pH. The eluted protein is diluted and further purified by ion exchange chromatography (for example, using a GE Healthcare SP Sepharose™-High Performance column in S-Buffer A (20 mM $NaH_2PO_4$ at pH 7.0), which is washed with several column volumes of S-Buffer and eluted with a 20 column volume linear gradient from 1 to 20% and a 20 column volume linear gradient from 20 to 50% S-Buffer B (20 mM $NaH_2PO_4$, 1 M NaCl, pH 7.0) followed by a step to 100% S-Buffer B at 5 ml/min).

The fractions are analyzed by Coomassie stained SDS-PAGE and fractions containing the bulk of the desired product pooled. The pooled material is then incubated with anti-FLAG® M2 Affinity Gel (Sigma A2220; Sigma-Aldrich, St. Louis Mo.) overnight. The resin is then washed with Tris-buffered saline and eluted with 100 mM HOAC, pH 3.5. The final pool is neutralized to pH 7.0 with 1 M Tris HCl, pH 8.0.

At any desired point, the material may be filtered through a 0.22 μm cellulose acetate filter; a spectral scan can be conducted on a sample, using a calculated molecular mass of 30,226 and a calculated extinction coefficient of 35,410 $M^{-1}$ $cm^{-1}$. The final pooled material may be concentrated if desired (for example, by using a Pall Macrosep® 10 kDa membrane at room temperature followed by filtration though a 0.22 μm cellulose acetate filter); another spectral scan may be conducted to verify concentration. The final product may then be analyzed by Coomassie stained SDS-PAGE (4-20% 1.0 mm tris-glycine gel) and SE-HPLC using a Phenomenx BioSep 3000 column (7.8×300 mm) in 50 mM $NaH_2PO_4$, 250 mM NaCl, pH 6.9.

N-terminal amino acid sequencing was used to verify that material purified in this manner contained PAR-2/Fc: FLAG®/fC heterodimers. Two sequences were detected: TIQGTNRSSKG (corresponding to amino acids 25 through 35 of SEQ ID NO:2), and DDYKDDDD (corresponding to SEQ ID NO:7). The ratio of two peptides was close to 1. Coomassie staining and SEC analysis confirmed that the material was PAR-2/Fc:FLAG®/Fc heterodimeric protein with undetectable levels of homodimeric proteins.

EXAMPLE 5

Analysis of PAR-2 antibodies by Western Blot

To analyze binding to uncleaved versus cleaved PAR-2, various amounts of purified uncleaved and clipped N-terminal PAR2-Fc are subjected to SDS-PAGE using 8-16% polyacrylamide gradient gels (Novex gels, Invitrogen Life Technologies) in a Tris-Glycine buffer system. Gel lanes containing See Blue standards (Novex, Invitrogen Life Technologies) for molecular weight identification are also included. Following electrophoresis, proteins are transferred from gels onto nitrocellulose membranes using a Novex XCell II Blot Module (Invitrogen Life Technologies). Membranes are blocked with 1:1, Odyssey blocking buffer, OBB, (LI-COR Biosciences):TBS (Tris Buffer Saline) overnight at 4 C with shaking. Antibodies to be analyzed are diluted in 1:1 OBB:TBS at a desired final concentration for 1 hr at room temperature. Membranes are washed extensively with 0.1% Tween 20 in TBS (3-4 changes of 100 ml over ~1 hr). Membranes are then exposed to the appropriate secondary antibody-Alexa680 (Molecular Probes, Invitrogen Life Technologies) conjugate (goat anti-rabbit IgG, or goat anti-mouse IgG) diluted 1:5000 in 1:1 (OBB:TBS) for 1 hr at room temperature. Membranes are washed as described above, and if desired, analyzed using a LI-COR Odyssey Infrared Imaging System (LI-COR Biosciences).

EXAMPLE 6

Binding Activity of PAR-2 Antibodies

This example describes binding activity as assessed by surface plasmon resonance using a BIAcore® biosensor (BIAcore International AB, Uppsala, Sweden). Briefly, anti-human Fc (or anti-murine Fc) is covalently coupled to biosensor chips (i.e., a CM5 chip) using a standard amine coupling procedure and reagents according to the manufacturer's instructions. PAR-2 antibody (human or murine, or a chimera, for example, SEQ ID NO:38) or a control antibody is injected over the immobilized anti-Fc, and varying amounts of PAR-2 (either homodimeric PAR-2-huFc or heterodimeric PAR-2-huFc/FLAG-huFc) are independently passed over an irrelevant antibody-coupled chip (negative control) as well as an anti-PAR-2-coated chip. Regeneration of the chip may be accomplished with one 10-microliter pulse of 100 mM phosphoric acid at 10 microliters/minute. All binding is performed in HBS (10 mM HEPES, 0.15 M NaCl, 3.4 mM EDTA, 0.02% NaN3, 0.005% surfactant P2O, pH 7.4) or equivalent.

EXAMPLE 7

Comparison of PAR-2 Antibodies

Several PAR-2 antibodies were tested in different assay formats; Table 2 summarizes the results. $IC_{50}$ values were determined in a FLIPR assay for Ca2+ mobilization described previously; binding to the upstream region of the cleavage site versus the downstream region of the cleavage site was determined using the Western blot assay described previously.

TABLE 2

| Antibody | IC$_{50}$ | Binding to Cleavage Site* | |
|---|---|---|---|
| | | Up stream | Down stream |
| 1A1 | 2 nM | xxx | — |
| 1B5 | 3 nM | xxx | — |
| 1C7 | 3 nM | xxx | — |
| 2C6 | >1 microM | — | xx |
| 9B12 | >1 microM | — | xx |
| 12D5 | >1 microM | — | xx |
| 13F2 | >1 microM | — | xx |

*In this Western blot, an antibody that binds downstream of the cleavage site will bind both full length and truncated amino-terminal PAR-2-Fc, whereas an antibody that binds upstream of the cleavage site will bind only the full-length PAR-2/Fc.

EXAMPLE 8

Adjuvant-induced Arthritis (AIA) Models

This example describes acute and chronic models of arthritis. In both models, animals are anesthetized, for example by Ketamine/Xylazine mixture (mouse mix or rat mix, respectively) or isoflurane for all intraarticular (IA), periarticular (PA) injections or intradermal (ID) injections.

Joint injections, IA or PA, are targeted at either knees or hind limb paws. PA injections are equally divided across four sites surrounding the joint of interest. Paw injections are administered ID into the plantar area of the hind paw. To serve as an internal control, one knee or hind-limb paw is injected with vehicle alone or sterile PBS. Preparation of the injection area includes shaving the joint area after animals are anesthetized, and scrubbing with an iodine solution followed by an alcohol disinfectant. All articular injections are given with a 30-gauge needle or equivalent, and when needed by a gastight (i.e., Hamilton) syringe, for small injection volumes (i.e. 10 microL).

For induction of acute AIA (aAIA), animals are injected on day zero (D0) with 1-4% lambda-carrageenan and 1-4% kaolin (C/K) by IA injection in saline. Concentrations of both compounds are dependent on intended disease severity. Total injection volumes for the inducing agent are between 10-20 microL for mice and 60-80 microL for rat. Both concentration and injection volume are consistent with published methodologies (*J Clin Invest.* 2003; 111(1):35-41, and *J Pharmacol Exp Ther.* 2006; 316(3):1017-24). Alternatively, specific PAR-2 peptide agonists, or other activators of inflammation (such as trypsin, or human beta-tryptase [*J Clin Invest.* 2003; 111(1):35-41, *J Pharmacol Exp Ther.* 2006; 316(3):1017-24, *J Pharmacol Sci.* 2005 97(1):38-42, and *Br J. Pharmacol.* 1999 127(5):1083-90]) or the equivalent, may be used. Concentrations used are selected for intended disease severity, and total injection volumes are appropriate to the animal being injected.

For induction of chronic AIA (cAIA), animals are injected day zero (D0) with 10-20 microL (mouse) and 60-80 microL (rat) of Freund's adjuvant with supplemented 10 mg/mL H37Ra *Mycobacterium tuberculosis* (M. tb.) [compete Freund's adjuvant; CFA] by IA injection, followed by 40-80 microL (mouse) and 120-200 microL (rat) by PA injection. Concentrations, injection volume, and injection regimen are consistent with published methodologies (*J Clin Invest.* 2003; 111(1):35-41). Adjuvant use follows internal IACUC Global Adjuvant Usage Standards, not exceeding 0.4 mL total for mice and 1 mL total for rats. All injections comply with internal Institutional Animal Care and Use Committee (IACUC) Dose Administration Standards, to include no more than 20 mL/kg IP, 1 mL/kg IA, and 5 mL/kg IV for mice and 10 mL/kg IP, 0.5 mL/kg IA, and 5 mL/g IV for rats.

Treatment intervention includes intraperitoneal (IP), intraarticular (IA), or intravenous (IV) administration routes; other suitable routes of administration may be used instead of or in addition to these. Any treatment regimen via IA injection is given at time other than D0, or at D0 but sequentially at a different injection site in the same joint (for example, a first injection into the interior aspect of the knee and a second injection into the exterior aspect.

For both acute and chronic AIA studies, caliper measurements of joint diameter are taken of all joints of interest prior to any injection. Tracking of disease may include caliper measurements of joint diameter as well as flexible tape measurements of joint circumference, and visual scoring. Alternative methods (i.e., use of a plethysmometer) may also be used. Severity of cAIA is scored by one or both of the criteria shown below:

| cAIA Joint Usage Criteria | cAIA Joint Appearance Criteria |
|---|---|
| 0 - Normal joint usage | 0 - Normal joint |
| 1 - Curling of toes | 1 - Redness/swelling in 1 to 3 digits |
| 2 - Aversion of the joint or paw | 2 - Redness/swelling in more than 3 digits, mild swelling extending into paw, swollen/red ankle, or mild swelling/redness of forepaw |
| 3 - Partial weight bearing | 3 - Swollen paw, mild to moderate redness |
| 4 - Non-weight bearing and guarding | 4 - Extreme redness and extreme swelling in entire paw |

In this manner, 6-8 week old Lewis rats were injected with C/K plus treatment (or control) in the left knee, and negative control in each right knee, as for the acute model. Joint thickness was measured at set time points after treatment, using an average of three caliper readings. The change in thickness of the left knee as compared to the right knee was expressed as percent change, and is shown in Table 3 below.

TABLE 3

| | 0 Hr | 2 Hr | 6 Hr | 24 Hr | 48 Hr | 72 Hr |
|---|---|---|---|---|---|---|
| PBS | 0.00 ± 0.00 | −0.26 ± 0.71 | 0.26 ± 0.65 | −0.84 ± 0.53 | −0.84 ± 0.55 | −0.48 ± 0.50 |
| C/K | 0.00 ± 0.00 | 3.88 ± 2.88 | 15.76 ± 1.74 | 17.51 ± 2.45 | 16.41 ± 1.39 | 8.07 ± 1.02 |
| SLIGRL | 0.00 ± 0.00 | 4.84** ± 0.87 | 8.02*** ± 1.17 | 5.68*** ± 1.07 | 3.47* ± 0.95 | 3.55* ± 0.81 |
| 1A1 | 0.00 ± 0.00 | 1.10 ± 1.13 | 4.12*** ± 1.29 | 3.57*** ± 1.20 | 4.70** ± 1.39 | 3.48 ± 0.66 |
| hIgG | 0.00 ± 0.00 | 4.80 ± 0.88 | 15.20 ± 2.91 | 13.77 ± 2.29 | 10.89 ± 1.30 | 5.95 ± 1.32 |

Values Represent Group Mean ± SEM. Statistics calculated by 2-way ANOVA with Bonferroni.
Monoclonal anitbody 1A1 was compared to hIgG; SLIGRL was conmpared to PBS.
*p < 0.05
**p < 0.01
***p < 0.001

These results demonstrate that an antagonistic anti-PAR-2 antibody reduces the inflammation observed in an adjuvant-induced arthritis model.

EXAMPLE 9

Adjuvant-Induced Arthritis (AIA) Models

This example describes the effects of PAR-2 antibodies on paw edema in an acute AIA model substantially as described previously. Briefly, 6-8 week old Sprague Dawley or Lewis rats (Charles River Laboratories, Wilmington, Mass.) were injected subcutaneously (SC) in the plantar region of the hind paw with 1% lambda carrageenan in one hind paw and control (saline) in the other. Blocking PAR-2 monoclonal antibody (1A1) or control (positive or negative control; see footnotes to Table 4) was administered intraperitoneally (IP) eighteen hours prior to adjuvant injection at 1.5 mg/rat (approximately 8-10 mg/kg), swelling was then measured by plethysomgraphy at selected time points. Data were expressed as volume of water in milliliters (mL) displaced per paw versus baseline measurements for that paw. Results of representative experiments are shown in Tables 4-5 below.

TABLE 4

Paw Edema in Lewis Rat

|  | 0 Hr | 2 Hr | 4 Hr | 6 Hr | 8 Hr |
|---|---|---|---|---|---|
| Saline | 0.00 ± 0.00 | 0.09 ± 0.05 | 0.03 ± 0.05 | 0.01 ± 0.04 | 0.01 ± 0.04 |
| Carrageenan | 0.00 ± 0.00 | 0.21 ± 0.05 | 0.24 ± 0.07 | 0.31 ± 0.04 | 0.46 ± 0.05 |
| 2B5[1] | 0.00 ± 0.00 | 0.13 ± 0.04 | 0.10 ± 0.02 | 0.06 ± 0.05 | 0.17 ± 0.09 |
| 1A1 | 0.00 ± 0.00 | 0.15 ± 0.06 | 0.09*** ± 0.04 | 0.14*** ± 0.07 | 0.30*** ± 0.06 |
| 2C6[2] | 0.00 ± 0.00 | 0.22 ± 0.02 | 0.22 ± 0.05 | 0.32 ± 0.06 | 0.51 ± 0.11 |

[1]2B5: Positive Control anti-PGE2, Cayman Chemical, Ann Arbor, Michigan
[2]2C6: Negative Control binding non-blocking anti-PAR2 mAb
* $p < 0.05$,
** $p < 0.01$,
*** $p < 0.001$ by 2-Way ANOVA with Bonferroni Post Test vs control.

TABLE 5

Paw Edema in Sprague Dawley Rat

|  | 0 Hr | 2 Hr | 4 Hr | 6 Hr |
|---|---|---|---|---|
| Saline | 0.00 ± 0.00 | 0.01 ± 0.08 | −0.01 ± 0.06 | −0.01 ± 0.04 |
| Carrageenan | 0.00 ± 0.00 | 0.61 ± 0.12 | 1.16 ± 0.13 | 1.36 ± 0.19 |
| Indomethacin[1] | 0.00 ± 0.00 | 0.26 ± 0.22 | 0.28 ± 0.08 | 0.49 ± 0.16 |
| 1A1 | 0.00 ± 0.00 | 0.15*** ± 0.05 | 0.45*** ± 0.08 | 0.49*** ± 0.08 |
| 2C6[2] | 0.00 ± 0.00 | 0.57 ± 0.08 | 1.06 ± 0.16 | 1.13 ± 0.08 |

[1]Indomethacin Positive Control at 5 mg/kg
[2]2C6: Negative Control binding non-blocking anti-PAR2 mAb
*$p < 0.05$,
**$p < 0.01$,
***$p < 0.001$ by 2-Way ANOVA with Bonferroni Post Test vs control.

In further experiments, a blocking PAR-2 antibody (1A1) significantly decreased paw swelling when administered IP but not when administered SC; subsequent pharmacokinetic analysis revealed that the bioavailability of SC administered 1 A1 was suboptimal in the paw edema study. Additionally, the inhibition of swelling by blocking PAR-2 antibody administered IP occurred in a dose-dependent manner. These results confirm previous findings that an antagonistic anti-PAR-2 antibody reduces the inflammation observed in an adjuvant-induced arthritis model.

EXAMPLE 10

Alteration in Proinflammatory Cytokines

Figure 1B:
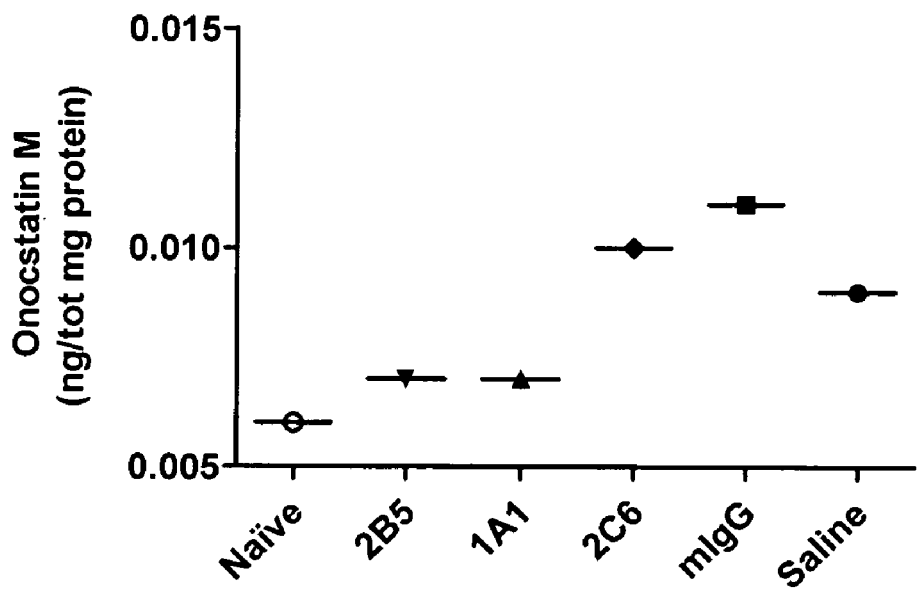
Figure 1C:
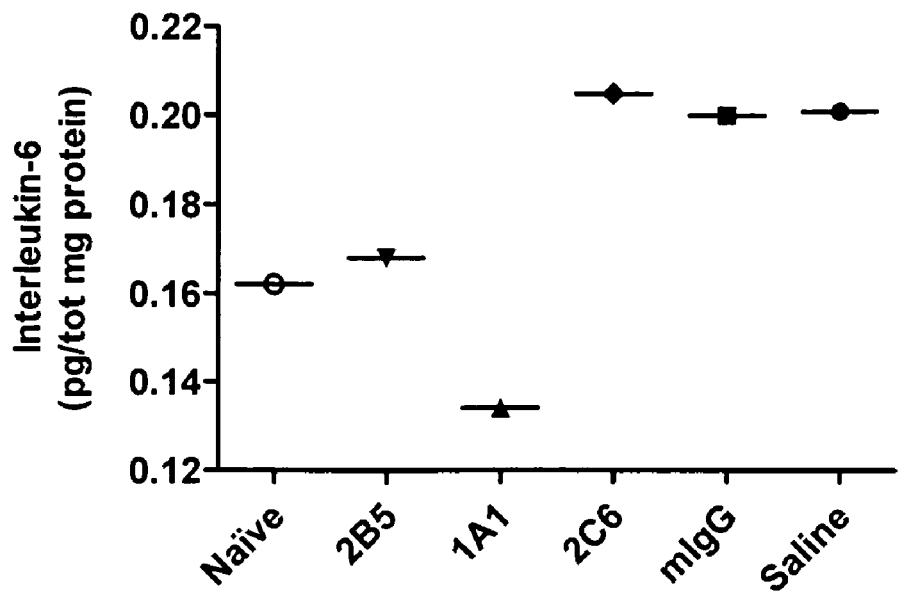
Figure 1D:
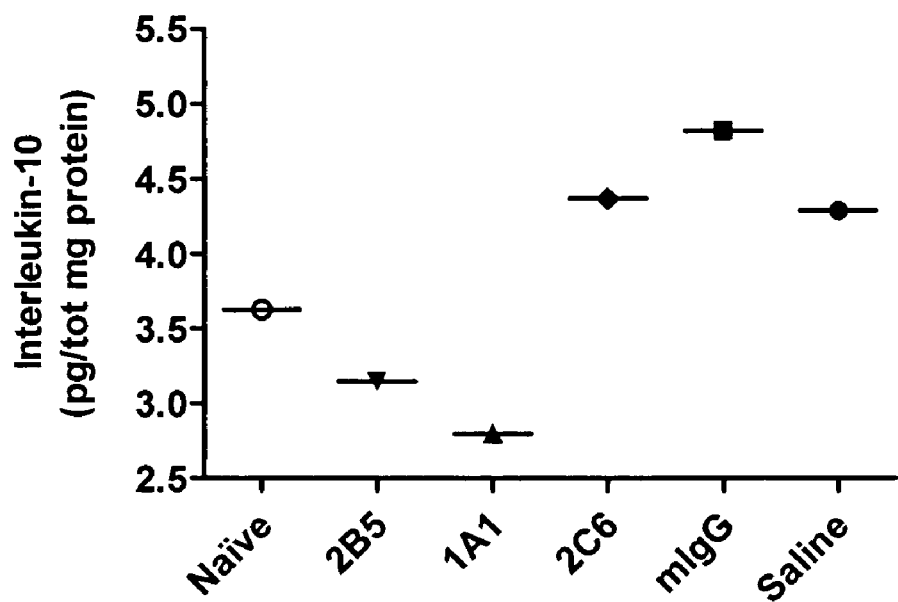

This example describes the effects of PAR-2 antibodies or benchmark positive control antibodies (i.e., anti-PGE2 2B5, from Cayman Chemical) on induction of proinflammatory cytokines. Briefly, tissue lysates from inflamed rat paws or control (naïve) paws were prepared by mincing in lysis buffer and placing on a Qiagen Tissue Lyser. Aliquots of samples were pooled, assessed for total protein by absorbance ($A_{280}$) using a micro-volume spectroscopy system (NanoDrop™, Thermo Scientific, Waltham Mass.), and submitted to Rules-Based Medicine, Inc. (Austin, Tex.) for multi-analyte profile (MAP) analysis on the Rodent Panel v2.0. Numerous analytes were altered with disease activity, comparisons shown included those differentiated by 1A1 and 2B5 treatment. Analytes were normalized to total protein (i.e. (pg, ng, microg)/mg tot protein); data are shown in FIG. 1. These results confirm literature findings that elevated release of pro-inflammatory mediators, such as cytokines and prostaglandin, are a hallmark of carageenan-induced edema. Lower levels of these factors observed in paw lysates in anti-PAR-2 antagonistic antibody treated animals suggests that these antibodies bind PAR-2 and significantly reduce subsequent production of pro-inflammatory mediators. The decrease in production of these analytes confirms the anti-inflammatory activity of PAR-2 neutralizing antibodies.

EXAMPLE 11

Binding Properties of Antigen-Binding Proteins

This example describes the analysis of the binding properties of PAR-2 antigen-binding proteins to cell surface expressed PAR-2 utilizing a Kinetic Exclusion Assay which measures binding events in solution phase and can be used to calculate $K_D$, $K_{on}$ and $K_{off}$ (KinExA®; Sapidyne Instruments, Boise, Id.), substantially as described previously by Xie et. al. *J. Imm, Methods* 304:1 (2005) and Rathanaswami et. al. *Anal. Biochem.* 373:52 (2008). Briefly, serial dilutions of cells expressing human PAR-2 (for example, CHO transfectants expressing human PAR-2 at the cell surface, obtainable by transfecting CHO cells with human full length PAR-2 cDNA encoding a polypeptide of SEQ ID NO:2) and control cells (i.e., non-transfected CHO cells) in a modified DMEM medium (phenol red free containing 10% heat inactivated FBS, 0.1 mM MEM non-essential amino acids, 1 mM sodium pyruvate, penicillin-streptomycin-glutamine, and 0.025% (w/w) sodium azide) are incubated with set amounts of antibody for 24 to 36 hours at 4 C with rotation. At the end of the incubation time, cells are pelleted by centrifugation, (i.e., for 4 minutes at 2000 rpm), and the supernatant containing unbound (free) antibody is removed. The free mAb is measured by KinExA® using the appropriate capture beads and Cy5-conjugated anti-human secondary antibodies, as described by Rathanaswami et al. *Biochem Biophys Research Commun:* 1004 (2005). The equilibrium dissociation constant ($K_D$) is obtained using KinExA® software and by "n-curve analysis" which fits all of the given curves to a single $K_D$ value simultaneously (Rathanswami et al. 2005 and Xie et al., supra).

The $K_D$ of certain PAR-2 antibodies was determined in this manner. As measured by KinExA®, the $K_D$ for the interaction of the anti-PAR-2 antibody 1A1 to cell surface expressed human PAR-2 is 62.8 pM with a 95% confidence interval of 24.8 to 134.7 pM (averaged for N=5 experiments). An initial analysis of antibody 1B5 in this system indicated a $K_D$ of 3.39 nM with a 95% confidence interval of 1.36 to 5.47 nM (N=2 experiments).

EXAMPLE 12

Induction of Collagen-induced Arthritis

This example describes a collagen-induced arthritis model utilizing rats. Porcine type II collagen (10 mg; Chondrex, Redmond, Wash.) is dissolved in 0.1N acetic acid (5 mL) two days prior to use on a rotating plate at 2-4 C. Subsequently, collagen is emulsified 1:1 with Freund's incomplete adjuvant (IFA; Difco, Detroit, Mich.) using an emulsification needle and glass syringes, yielding a final concentration of 1 mg/mL. Disease is induced in 8-week old female Lewis rats (Charles River, Wilmington, Mass.) by intradermal injection of emulsified collagen in IFA at 10 different sites (100 microL per site) over the back. The clinical onset of arthritis varies, usually between 10 to 12 days, as indicated by hind paw swelling and ambulatory difficulties. Prior to collagen immunization rats are randomized to treatment groups and therapy is initiated with an i.p. administration of PAR-2 neutralizing antibody, control antibodies (i.e., PAR-2 non-blocking antibodies) or vehicle control (A5Su). A second dose of the antibodies and vehicle is administered the day before onset, Day 9.

Progression of inflammation during the study is assessed clinically by the intermittent measurement of hind paw diameter using calipers Readings are taken at the tibiotarsal (ankle) joint prior to induction of arthritis, at the day of onset (Day 10), on days 11-17, and at necropsy (Day 18). Inhibition of paw inflammation is calculated based on the area under the curve (AUC) according to the formula:

[(Vehicle treated CIA−Treated CIA)/(Vehicle treated CIA)]×100

In addition, total body weight is determined daily during the treatment regimen as a supplemental endpoint because body weight loss parallels the progression of joint inflammation in this arthritis model.

At study termination, ankle joints may be evaluated for loss of bone mineral density (BMD) as well as for changes in the phosphorylation of mitogen-activated protein kinase-activated kinase-2 (MAPKAPK-2 or MK-2). BMD is examined using dual-energy x-ray absorptiometry (DEXA) at a suitable time point after necropsy. Hind paws are removed at the fur line (just proximal to the ankle [hock]), immersed in 70% ethanol and stored at room temperature until the BMD is determined. The joints are then scanned in horizontal orientation using a fan beam X-ray densitometer (Model QDR-4500A; Hologic, Waltham, Mass.) substantially as described by (Feige et al., *Cell Mol Life Sci* 57:1457; 2000). After the scan, a rectangular box (29×25 mm) centered at the calcaneus is positioned to delineate the site to be analyzed, and algorithms validated for the instrumentation used (for example, Hologic software) are used to calculate bone area, bone mineral content, and bone mineral density. For the phosphor analysis, one ankle is frozen in liquid N2 for crushing into a protein powder that is run on a Western blot using a commercially available MK-2 assay.

Each reference cited herein is incorporated by reference in its entirety for all that it teaches and for all purposes.

What is claimed is:

1. An isolated monoclonal antibody or antigen binding portion thereof, having a heavy chain and a light chain, the heavy chain comprising a variable region that is at least 95% identical to SEQ ID NO:9, and the light chain comprising a variable region that is at least 95% identical to SEQ ID NO:11 wherein the antibody or an antigen binding portion thereof binds to Protease Activated Receptor-2 (PAR-2) upstream of the proteolytic cleavage site.

2. An isolated monoclonal antibody or antigen binding portion thereof, having a heavy chain and a light chain, wherein the light chain variable region has the amino acid sequence of SEQ ID NO:39, and the heavy chain variable region has the amino acid sequence of SEQ ID NO:40, further wherein the antibody or an antigen bindin aportion thereof binds to Protease Activated Receptor-2 (PAR-2) upstream of the proteolytic cleavage sit.

3. An isolated monoclonal antibody or antigen binding portion thereof, having a heavy chain and a light chain, the heavy chain comprising a variable region, and the light chain comprising a variable region, wherein the light chain variable region has an amino acid sequence selected from the group of amino acid sequences consisting of SEQ ID NO:11, SEQ ID NO:15 and SEQ ID NO:19, and the heavy chain variable region has an amino acid sequence selected from the group of amino acid sequences consisting of SEQ ID NO:9, SEQ ID NO:13 and SEQ ID NO:17, further wherein the *antibody* or antigen binding portion thereof binds to P*rotease* A*ctivated* R*eceptor*-2 (PAR-2) upstream of the *proteolytic* cleavage *site*.

4. An isolated antibody or antigen binding portion thereof selected from the group consisting of
   a) An antibody or antigen binding portion thereof comprising a light chain variable region having the amino acid sequence of SEQ ID NO:11, and heavy chain variable region having the amino acid sequence of SEQ ID NO:9;
   b) An antibody or antigen binding portion thereof comprising a light chain variable region having the amino acid sequence of SEQ ID NO:15, and heavy chain variable region having the amino acid sequence of SEQ ID NO:13; and
   c) antibody or antigen binding portion thereof comprising a light chain variable region having the amino acid sequence of SEQ ID NO:19, and heavy chain variable region having the amino acid sequence of SEQ ID NO:17.

5. A composition comprising the isolated antibody or antigen binding portion thereof of any one of claims 1 through 4 or claim 3 and a physiologically acceptable diluent, excipient or carrier.

* * * * *

UNITED STATES PATENT AND TRADEMARK OFFICE
CERTIFICATE OF CORRECTION

PATENT NO.         : 8,357,367 B2
APPLICATION NO.    : 12/215304
DATED              : January 22, 2013
INVENTOR(S)        : G. Duke Virca et al.

It is certified that error appears in the above-identified patent and that said Letters Patent is hereby corrected as shown below:

In the Claims

Claim 2, Column 85, line 15, "antigen bindin aportion" should be --antigen binding portion--.

Claim 2, Column 85, line 17, "cleavage sit" should be --cleavage site--.

Signed and Sealed this
Seventeenth Day of February, 2015

Michelle K. Lee
*Deputy Director of the United States Patent and Trademark Office*

SEQUENCE LISTING

```
<160> NUMBER OF SEQ ID NOS: 43

<210> SEQ ID NO 1
<211> LENGTH: 1194
<212> TYPE: DNA
<213> ORGANISM: Homo sapiens
<220> FEATURE:
<221> NAME/KEY: CDS
<222> LOCATION: (1)..(1191)

<400> SEQUENCE: 1 atg cgg agc ccc agc gcg gcg tgg ctg ctg ggg gcc gcc atc ctg cta      48
```

```
         Met Arg Ser Pro Ser Ala Ala Trp Leu Leu Gly Ala Ala Ile Leu Leu
         1               5                   10                  15 gca gcc tct ctc tcc tgc agt ggc acc atc caa gga acc aat aga tcc           96
Ala Ala Ser Leu Ser Cys Ser Gly Thr Ile Gln Gly Thr Asn Arg Ser
            20                  25                  30 tct aaa gga aga agc ctt att ggt aag gtt gat ggc aca tcc cac gtc          144
Ser Lys Gly Arg Ser Leu Ile Gly Lys Val Asp Gly Thr Ser His Val
        35                  40                  45 act gga aaa gga gtt aca gtt gaa aca gtc ttt tct gtg gat gag ttt          192
Thr Gly Lys Gly Val Thr Val Glu Thr Val Phe Ser Val Asp Glu Phe
    50                  55                  60 tct gca tct gtc ctc act gga aaa ctg acc act gtc ttc ctt cca att          240
Ser Ala Ser Val Leu Thr Gly Lys Leu Thr Thr Val Phe Leu Pro Ile
65              70                  75                  80 gtc tac aca att gtg ttt gtg gtg ggt ttg cca agt aac ggc atg gcc          288
Val Tyr Thr Ile Val Phe Val Val Gly Leu Pro Ser Asn Gly Met Ala
                85                  90                  95 ctg tgg gtc ttt ctt ttc cga act aag aag aag cac cct gct gtg att          336
Leu Trp Val Phe Leu Phe Arg Thr Lys Lys Lys His Pro Ala Val Ile
            100                 105                 110 tac atg gcc aat ctg gcc ttg gct gac ctc ctc tct gtc atc tgg ttc          384
Tyr Met Ala Asn Leu Ala Leu Ala Asp Leu Leu Ser Val Ile Trp Phe
        115                 120                 125 ccc ttg aag att gcc tat cac ata cat ggc aac aac tgg att tat ggg          432
Pro Leu Lys Ile Ala Tyr His Ile His Gly Asn Asn Trp Ile Tyr Gly
    130                 135                 140 gaa gct ctt tgt aat gtg ctt att ggc ttt ttc tat ggc aac atg tac          480
Glu Ala Leu Cys Asn Val Leu Ile Gly Phe Phe Tyr Gly Asn Met Tyr
145                 150                 155                 160 tgt tcc att ctc ttc atg acc tgc ctc agt gtg cag agg tat tgg gtc          528
Cys Ser Ile Leu Phe Met Thr Cys Leu Ser Val Gln Arg Tyr Trp Val
                165                 170                 175 atc gtg aac ccc atg ggg cac tcc agg aag aag gca aac att gcc att          576
Ile Val Asn Pro Met Gly His Ser Arg Lys Lys Ala Asn Ile Ala Ile
            180                 185                 190 ggc atc tcc ctg gca ata tgg ctg ctg att ctg ctg gtc acc atc cct          624
Gly Ile Ser Leu Ala Ile Trp Leu Leu Ile Leu Leu Val Thr Ile Pro
        195                 200                 205 ttg tat gtc gtg aag cag acc atc ttc att cct gcc ctg aac atc acg          672
Leu Tyr Val Val Lys Gln Thr Ile Phe Ile Pro Ala Leu Asn Ile Thr
    210                 215                 220 acc tgt cat gat gtt ttg cct gag cag ctc ttg gtg gga gac atg ttc          720
Thr Cys His Asp Val Leu Pro Glu Gln Leu Leu Val Gly Asp Met Phe
225                 230                 235                 240 aat tac ttc ctc tct ctg gcc att ggg gtc ttt ctg ttc cca gcc ttc          768
Asn Tyr Phe Leu Ser Leu Ala Ile Gly Val Phe Leu Phe Pro Ala Phe
                245                 250                 255 ctc aca gcc tct gcc tat gtg ctg atg atc aga atg ctg cga tct tct          816
Leu Thr Ala Ser Ala Tyr Val Leu Met Ile Arg Met Leu Arg Ser Ser
            260                 265                 270 gcc atg gat gaa aac tca gag aag aaa agg aag agg gcc atc aaa ctc          864
Ala Met Asp Glu Asn Ser Glu Lys Lys Arg Lys Arg Ala Ile Lys Leu
        275                 280                 285 att gtc act gtc ctg gcc atg tac ctg atc tgc ttc act cct agt aac          912
Ile Val Thr Val Leu Ala Met Tyr Leu Ile Cys Phe Thr Pro Ser Asn
    290                 295                 300 ctt ctg ctt gtg gtg cat tat ttt ctg att aag agc cag ggc cag agc          960
Leu Leu Leu Val Val His Tyr Phe Leu Ile Lys Ser Gln Gly Gln Ser
305                 310                 315                 320 cat gtc tat gcc ctg tac att gta gcc ctc tgc ctc tct acc ctt aac         1008
```

```
His Val Tyr Ala Leu Tyr Ile Val Ala Leu Cys Leu Ser Thr Leu Asn
                325                 330                 335 agc tgc atc gac ccc ttt gtc tat tac ttt gtt tca cat gat ttc agg    1056
Ser Cys Ile Asp Pro Phe Val Tyr Tyr Phe Val Ser His Asp Phe Arg
                340                 345                 350 gat cat gca aag aac gct ctc ctt tgc cga agt gtc cgc act gta aag    1104
Asp His Ala Lys Asn Ala Leu Leu Cys Arg Ser Val Arg Thr Val Lys
                355                 360                 365 cag atg caa gta tcc ctc acc tca aag aaa cac tcc agg aaa tcc agc    1152
Gln Met Gln Val Ser Leu Thr Ser Lys Lys His Ser Arg Lys Ser Ser
        370                 375                 380 tct tac tct tca agt tca acc act gtt aag acc tcc tat tga            1194
Ser Tyr Ser Ser Ser Ser Thr Thr Val Lys Thr Ser Tyr
385                 390                 395

<210> SEQ ID NO 2
<211> LENGTH: 397
<212> TYPE: PRT
<213> ORGANISM: Homo sapiens

<400> SEQUENCE: 2

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
                20                  25                  30

Ser Lys Gly Arg Ser Leu Ile Gly Lys Val Asp Gly Thr Ser His Val
            35                  40                  45

Thr Gly Lys Gly Val Thr Val Glu Thr Val Phe Ser Val Asp Glu Phe
        50                  55                  60

Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys Lys His Pro Ala Val Ile
                100                 105                 110

Tyr Met Ala Asn Leu Ala Leu Ala Asp Leu Leu Ser Val Ile Trp Phe
            115                 120                 125

Pro Leu Lys Ile Ala Tyr His Ile His Gly Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
                180                 185                 190

Gly Ile Ser Leu Ala Ile Trp Leu Leu Ile Leu Val Thr Ile Pro
            195                 200                 205

Leu Tyr Val Val Lys Gln Thr Ile Phe Ile Pro Ala Leu Asn Ile Thr
        210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
                260                 265                 270

Ala Met Asp Glu Asn Ser Glu Lys Lys Arg Lys Arg Ala Ile Lys Leu
            275                 280                 285
```

```
Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Tyr Phe Val Ser Asp Phe Arg
                340                 345                 350

Asp His Ala Lys Asn Ala Leu Leu Cys Arg Ser Val Arg Thr Val Lys
                355                 360                 365

Gln Met Gln Val Ser Leu Thr Ser Lys Lys His Ser Arg Lys Ser Ser
370                 375                 380

Ser Tyr Ser Ser Ser Thr Thr Val Lys Thr Ser Tyr
385                 390                 395

<210> SEQ ID NO 3
<211> LENGTH: 399
<212> TYPE: PRT
<213> ORGANISM: Mus musculus

<400> SEQUENCE: 3

Met Arg Ser Leu Ser Leu Ala Trp Leu Leu Gly Gly Ile Thr Leu Leu
1               5                   10                  15

Ala Ala Ser Val Ser Cys Ser Arg Thr Glu Asn Leu Ala Pro Gly Arg
                20                  25                  30

Asn Asn Ser Lys Gly Arg Ser Leu Ile Gly Arg Leu Gly Thr Gln Pro
            35                  40                  45

Pro Ile Thr Gly Lys Gly Val Pro Val Glu Pro Gly Phe Ser Ile Asp
    50                  55                  60

Glu Phe Ser Ala Ser Ile Leu Thr Gly Lys Leu Thr Thr Val Phe Leu
65                  70                  75                  80

Pro Val Val Tyr Ile Ile Val Phe Val Ile Gly Leu Pro Ser Asn Gly
                    85                  90                  95

Met Ala Leu Trp Ile Phe Leu Phe Arg Thr Lys Lys Lys His Pro Ala
                100                 105                 110

Val Ile Tyr Met Ala Asn Leu Ala Leu Ala Asp Leu Leu Ser Val Ile
                115                 120                 125

Trp Phe Pro Leu Ala Ile Ala Tyr His Leu His Gly Asn Asn Trp Val
130                 135                 140

Tyr Gly Glu Ala Leu Cys Lys Val Leu Ile Gly Phe Phe Tyr Gly Asn
145                 150                 155                 160

Met Tyr Cys Ser Ile Leu Phe Met Thr Cys Leu Ser Val Gln Arg Tyr
                165                 170                 175

Trp Val Ile Val Asn Pro Met Gly His Pro Arg Lys Lys Ala Asn Ile
                180                 185                 190

Ala Val Gly Val Ser Leu Ala Ile Trp Leu Leu Ile Phe Leu Val Thr
            195                 200                 205

Ile Pro Leu Tyr Val Met Lys Gln Thr Ile Tyr Ile Pro Ala Leu Asn
    210                 215                 220

Ile Thr Thr Cys His Asp Val Leu Pro Glu Glu Val Leu Val Gly Asp
225                 230                 235                 240

Met Phe Asn Tyr Phe Leu Ser Leu Ala Ile Gly Val Phe Leu Phe Pro
                245                 250                 255

Ala Ile Leu Thr Ala Ser Ala Tyr Val Leu Met Ile Lys Thr Leu Arg
                260                 265                 270
```

-continued

Ser Ser Ala Met Asp Glu His Ser Glu Lys Lys Arg Gln Arg Ala Ile
            275                 280                 285

Arg Leu Ile Ile Thr Val Leu Ala Met Tyr Phe Ile Cys Phe Ala Pro
        290                 295                 300

Ser Asn Leu Leu Leu Val Val His Tyr Phe Leu Ile Lys Thr Gln Arg
305                 310                 315                 320

Gln Ser His Val Tyr Ala Leu Tyr Leu Val Ala Leu Cys Leu Ser Thr
                325                 330                 335

Leu Asn Ser Cys Ile Asp Pro Phe Val Tyr Tyr Phe Val Ser Lys Asp
            340                 345                 350

Phe Arg Asp His Ala Arg Asn Ala Leu Leu Cys Arg Ser Val Arg Thr
        355                 360                 365

Val Asn Arg Met Gln Ile Ser Leu Ser Ser Asn Lys Phe Ser Arg Lys
    370                 375                 380

Ser Gly Ser Tyr Ser Ser Ser Thr Ser Val Lys Thr Ser Tyr
385                 390                 395

<210> SEQ ID NO 4
<211> LENGTH: 397
<212> TYPE: PRT
<213> ORGANISM: Rattus rattus

<400> SEQUENCE: 4

Met Arg Ser Leu Ser Leu Ala Trp Leu Leu Gly Gly Ile Thr Leu Leu
1               5                   10                  15

Ala Ala Ser Ala Ser Cys Asn Arg Thr Val Asn Ala Pro Gly Pro Asn
            20                  25                  30

Ser Lys Gly Arg Ser Leu Ile Gly Arg Leu Asp Thr Pro Pro Pro Ile
        35                  40                  45

Thr Gly Lys Gly Ala Pro Val Glu Pro Gly Phe Ser Val Asp Glu Phe
    50                  55                  60

Ser Ala Ser Val Leu Thr Gly Lys Leu Thr Thr Val Phe Leu Pro Val
65                  70                  75                  80

Ile Tyr Ile Ile Val Phe Val Ile Gly Leu Pro Ser Asn Gly Met Ala
                85                  90                  95

Leu Trp Val Phe Phe Phe Arg Thr Lys Lys Lys His Pro Ala Val Ile
            100                 105                 110

Tyr Met Ala Asn Leu Ala Leu Ala Asp Leu Leu Ser Val Ile Trp Phe
        115                 120                 125

Pro Leu Lys Ile Ser Tyr His Leu His Gly Asn Asp Trp Thr Tyr Gly
    130                 135                 140

Asp Ala Leu Cys Lys Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Arg Ala Asn Ile Ala Val
            180                 185                 190

Gly Val Ser Leu Ala Ile Trp Leu Leu Ile Phe Leu Val Thr Ile Pro
        195                 200                 205

Leu Tyr Val Met Arg Gln Thr Ile Tyr Ile Pro Ala Leu Asn Ile Thr
    210                 215                 220

Thr Cys His Asp Val Leu Pro Glu Glu Val Leu Val Gly Asp Met Phe
225                 230                 235                 240

Ser Tyr Phe Leu Ser Leu Ala Ile Gly Val Phe Leu Phe Pro Ala Leu
                245                 250                 255

```
Leu Thr Ala Ser Ala Tyr Val Leu Met Ile Lys Thr Leu Arg Ser Ser
            260                 265                 270

Ala Met Asp Glu His Ser Glu Lys Lys Arg Arg Ala Ile Arg Leu
        275                 280                 285

Ile Ile Thr Val Leu Ser Met Tyr Phe Ile Cys Phe Ala Pro Ser Asn
    290                 295                 300

Val Leu Val Val His Tyr Phe Leu Ile Lys Ser Gln Arg Gln Ser
305                 310                 315                 320

His Val Tyr Ala Leu Tyr Leu Val Ala Leu Cys Leu Ser Thr Leu Asn
                325                 330                 335

Ser Cys Ile Asp Pro Phe Val Tyr Phe Val Ser Lys Asp Phe Arg
            340                 345                 350

Asp Gln Ala Arg Asn Ala Leu Leu Cys Arg Ser Val Arg Thr Val Lys
                355                 360                 365

Arg Met Gln Ile Ser Leu Thr Ser Asn Lys Phe Ser Arg Lys Ser Ser
    370                 375                 380

Ser Tyr Ser Ser Ser Ser Thr Ser Val Lys Thr Ser Tyr
385                 390                 395

<210> SEQ ID NO 5
<211> LENGTH: 903
<212> TYPE: DNA
<213> ORGANISM: Homo sapiens
<220> FEATURE:
<221> NAME/KEY: CDS
<222> LOCATION: (1)..(900)

<400> SEQUENCE: 5 atg cgg agc ccc agc gcg gcg tgg ctg ctg ggg gcc gcc atc ctg cta      48
Met Arg Ser Pro Ser Ala Ala Trp Leu Leu Gly Ala Ala Ile Leu Leu
1               5                   10                  15 gca gcc tct ctc tcc tgc agt ggc acc atc caa gga acc aat aga tcc      96
Ala Ala Ser Leu Ser Cys Ser Gly Thr Ile Gln Gly Thr Asn Arg Ser
                20                  25                  30 tct aaa gga aga agc ctt att ggt aag gtt gat ggc aca tcc cac gtc     144
Ser Lys Gly Arg Ser Leu Ile Gly Lys Val Asp Gly Thr Ser His Val
            35                  40                  45 act gga aaa gga gtt aca gtt gaa aca gtc ttt tct gtg gat gag ttt     192
Thr Gly Lys Gly Val Thr Val Glu Thr Val Phe Ser Val Asp Glu Phe
        50                  55                  60 tct gca tct gtc ctc act gga aaa gtc gac aaa act cac aca tgc cca     240
Ser Ala Ser Val Leu Thr Gly Lys Val Asp Lys Thr His Thr Cys Pro
65                  70                  75                  80 ccg tgc cca gca cct gaa ctc ctg ggg gga ccg tca gtc ttc ctc ttc     288
Pro Cys Pro Ala Pro Glu Leu Leu Gly Gly Pro Ser Val Phe Leu Phe
                85                  90                  95 ccc cca aaa ccc aag gac acc ctc atg atc tcc cgg acc cct gag gtc     336
Pro Pro Lys Pro Lys Asp Thr Leu Met Ile Ser Arg Thr Pro Glu Val
                100                 105                 110 aca tgc gtg gtg gtg gac gtg agc cac gaa gac cct gag gtc aag ttc     384
Thr Cys Val Val Val Asp Val Ser His Glu Asp Pro Glu Val Lys Phe
            115                 120                 125 aac tgg tac gtg gac ggc gtg gag gtg cat aat gcc aag aca aag ccg     432
Asn Trp Tyr Val Asp Gly Val Glu Val His Asn Ala Lys Thr Lys Pro
        130                 135                 140 cgg gag gag cag tac aac agc acg tac cgt gtg gtc agc gtc ctc acc     480
Arg Glu Glu Gln Tyr Asn Ser Thr Tyr Arg Val Val Ser Val Leu Thr
145                 150                 155                 160 gtc ctg cac cag gac tgg ctg aat ggc aag gag tac aag tgc aag gtc     528
```

```
                Val Leu His Gln Asp Trp Leu Asn Gly Lys Glu Tyr Lys Cys Lys Val
                                165                 170                 175 tcc aac aaa gcc ctc cca gcc ccc atc gag aaa acc atc tcc aaa gcc              576
Ser Asn Lys Ala Leu Pro Ala Pro Ile Glu Lys Thr Ile Ser Lys Ala
            180                 185                 190 aaa ggg cag ccc cga gag cca cag gtg tac acc ctg ccc cca tcc cgg              624
Lys Gly Gln Pro Arg Glu Pro Gln Val Tyr Thr Leu Pro Pro Ser Arg
        195                 200                 205 gat gag ctg acc aag aac cag gtc agc ctg acc tgc ctg gtc aaa ggc              672
Asp Glu Leu Thr Lys Asn Gln Val Ser Leu Thr Cys Leu Val Lys Gly
        210                 215                 220 ttc tat ccc agc gac atc gcc gtg gag tgg gag agc aat ggg cag ccg              720
Phe Tyr Pro Ser Asp Ile Ala Val Glu Trp Glu Ser Asn Gly Gln Pro
225                 230                 235                 240 gag aac aac tac aag acc acg cct ccc gtg ctg gac tcc gac ggc tcc              768
Glu Asn Asn Tyr Lys Thr Thr Pro Pro Val Leu Asp Ser Asp Gly Ser
                245                 250                 255 ttc ttc ctc tac agc aag ctc acc gtg gac aag agc agg tgg cag cag              816
Phe Phe Leu Tyr Ser Lys Leu Thr Val Asp Lys Ser Arg Trp Gln Gln
            260                 265                 270 ggg aac gtc ttc tca tgc tcc gtg atg cat gag gct ctg cac aac cac              864
Gly Asn Val Phe Ser Cys Ser Val Met His Glu Ala Leu His Asn His
        275                 280                 285 tac acg cag aag agc ctc tcc ctg tct ccg ggt aaa tga                          903
Tyr Thr Gln Lys Ser Leu Ser Leu Ser Pro Gly Lys
        290                 295                 300

<210> SEQ ID NO 6
<211> LENGTH: 300
<212> TYPE: PRT
<213> ORGANISM: Homo sapiens

<400> SEQUENCE: 6

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Val Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
```

```
                    195                 200                 205
Asp Glu Leu Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
290                 295                 300

<210> SEQ ID NO 7
<211> LENGTH: 8
<212> TYPE: PRT
<213> ORGANISM: Artificial
<220> FEATURE:
<223> OTHER INFORMATION: FLAG? Peptide

<400> SEQUENCE: 7

Asp Tyr Lys Asp Asp Asp Asp Lys
1               5

<210> SEQ ID NO 8
<211> LENGTH: 378
<212> TYPE: DNA
<213> ORGANISM: Homo sapiens

<400> SEQUENCE: 8
gaggtgcagc tggtgcagtc tggagcagag gtgaaaaagc ccggggagtc tctgaagatc      60
tcctgtaagg gttctggata caactttatc agccactgga tcggctgggt gcgccagatg     120
cccgggaaag gcctggagtg gatggggatg atctatcctg gtgactctga taccagatac     180
agcccgtcct tccaaggcca ggtcaccatc tcagccgaca gtccatcaa taccgcctac     240 ctgcagtgga agcctgaa ggcctcggac accgccatgt atttctgtgc gagacatgga     300
ggtataactg gaactacctt ctactacgac ttcggtatgg acgtctgggg ccaagggacc     360
acggtcaccg tctcctca                                                  378

<210> SEQ ID NO 9
<211> LENGTH: 126
<212> TYPE: PRT
<213> ORGANISM: Homo sapiens

<400> SEQUENCE: 9

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Ile Ser His
            20                  25                  30

Trp Ile Gly Trp Val Arg Gln Met Pro Gly Lys Gly Leu Glu Trp Met
        35                  40                  45

Gly Met Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Arg Ser Leu Lys Ala Ser Asp Thr Ala Met Tyr Phe Cys
                85                  90                  95
```

Ala Arg His Gly Gly Ile Thr Gly Thr Thr Phe Tyr Tyr Asp Phe Gly
            100                 105                 110

Met Asp Val Trp Gly Gln Gly Thr Thr Val Thr Val Ser Ser
            115                 120                 125

<210> SEQ ID NO 10
<211> LENGTH: 321
<212> TYPE: DNA
<213> ORGANISM: Homo sapiens

<400> SEQUENCE: 10
tcctatgagc tgacacagcc accctcggtg tcagtgtccc caggacagac ggccaggatc    60
acctgctctg gagatgcatt gccaaagcaa tatgcttctt ggtaccagca gaagccaggc   120
caggcccctc tattggtgat atatagagac agtgagaggc cctcaggct ccctgagcga    180 ttctctggct ccagctcagg gacaacagtc acgttgacca tcagtggagt ccaggcagaa   240
gacgaggcta actattactg tcaatcggca gacagcggtg ttcttatgt cttcggcact    300 gggaccaagg tcaccgtcct a                                             321

<210> SEQ ID NO 11
<211> LENGTH: 107
<212> TYPE: PRT
<213> ORGANISM: Homo sapiens

<400> SEQUENCE: 11

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Ser Trp Tyr Gln Gln Lys Pro Gly Gln Ala Pro Leu Leu Val Ile Tyr
        35                  40                  45

Arg Asp Ser Glu Arg Pro Ser Gly Leu Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Gly Gly Ser Tyr
                85                  90                  95

Val Phe Gly Thr Gly Thr Lys Val Thr Val Leu
            100                 105

<210> SEQ ID NO 12
<211> LENGTH: 378
<212> TYPE: DNA
<213> ORGANISM: Homo sapiens

<400> SEQUENCE: 12
gaggtgcagc tggtgcagtc tggagcagag gtgaaaaagt ccggggagtc tctgaagatc    60
tcctgtaagg gttctggata cagctttttcc aactactgga tcggctgggt gcgccagatg  120
cccgggaaag gcctggagtg gatgggaatc atctatcctg gtgactctga taccagatac   180
agcccgtcct tccagggcca ggtcaccatc tcagccgaca gtccatcag aaccgcctac    240 ctacagtgga gcagtttgaa ggcctcggac accgccatgt attactgtgc gagacataaa   300
ggtataactg gaactacctt ctactacgac tacggcatgg acgtctgggg ccaagggacc   360
acggtcaccg tctcctca                                                 378

<210> SEQ ID NO 13

```
<211> LENGTH: 126
<212> TYPE: PRT
<213> ORGANISM: Homo sapiens

<400> SEQUENCE: 13

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Lys Gly Ile Thr Gly Thr Thr Phe Tyr Tyr Asp Tyr Gly
            100                 105                 110

Met Asp Val Trp Gly Gln Gly Thr Thr Val Thr Val Ser Ser
        115                 120                 125

<210> SEQ ID NO 14
<211> LENGTH: 321
<212> TYPE: DNA
<213> ORGANISM: Homo sapiens

<400> SEQUENCE: 14
tcctatgagt tgacacagcc accctcggtg tcagtgtccc caggacagac ggccaggatc      60
acctgctctg gagaagcttt gccaaaacaa tatgcttctt ggtaccagca gaagccaggc     120
caggcccctg tcttggtgat atatagagac actgagaggc cctcagggat ccctgagcga     180
ttctctggct ccagctcagg gacaacagtc acgttgacca tcagtggagt ccaggcagaa     240
gacgaggctg actattactg tcaatcagca gacagcaatg gtgcttatgt cttcggaact     300
gggaccaggg tcaccgtcct a                                                321

<210> SEQ ID NO 15
<211> LENGTH: 107
<212> TYPE: PRT
<213> ORGANISM: Homo sapiens

<400> SEQUENCE: 15

Ser Tyr Glu Leu Thr Gln Pro Pro Ser Val Ser Val Ser Pro Gly Gln
1               5                   10                  15

Thr Ala Arg Ile Thr Cys Ser Gly Glu Ala Leu Pro Lys Gln Tyr Ala
            20                  25                  30

Ser Trp Tyr Gln Gln Lys Pro Gly Gln Ala Pro Val Leu Val Ile Tyr
        35                  40                  45

Arg Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Asn Gly Ala Tyr
                85                  90                  95

Val Phe Gly Thr Gly Thr Arg Val Thr Val Leu
            100                 105
```

```
<210> SEQ ID NO 16
<211> LENGTH: 378
<212> TYPE: DNA
<213> ORGANISM: Homo sapiens

<400> SEQUENCE: 16
gaggtgcagt tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatgggaatc atctatcctg gtgactctga taccagatac     180
agcccgtcct tccaaggcca ggtcaccatc tcagccgaca gtccatcag aaccgcctac      240 ctacagtgga gcagtttgaa ggcctcggac accgccatgt attactgtgc gagacataaa     300
ggtataactg gaactacctt ctactacgac tacggcatgg acgtctgggg ccaagggacc     360
acggtcaccg tctcctca                                                    378

<210> SEQ ID NO 17
<211> LENGTH: 126
<212> TYPE: PRT
<213> ORGANISM: Homo sapiens

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Lys Gly Ile Thr Gly Thr Thr Phe Tyr Tyr Asp Tyr Gly
            100                 105                 110

Met Asp Val Trp Gly Gln Gly Thr Thr Val Thr Val Ser Ser
        115                 120                 125

<210> SEQ ID NO 18
<211> LENGTH: 321
<212> TYPE: DNA
<213> ORGANISM: Homo sapiens

<400> SEQUENCE: 18
tcctatgagt tgacacagcc accctcggtg tcagtgtccc caggacagac ggccaggatc      60
acctgctctg gagaagcttt gccaaagcaa tatgcttctt ggtaccagca gaagccaggc     120
caggcccctg tcttggtgat atataaagac agtgagaggc cctcagggat ccctgagcga     180
ttctctggct ccagctcagg gacaacagtc acgttgacca tcagtggagt ccaggcagaa     240
gacgaggctg actattactg tcaatcagca gacagcaatg tgcttatgt cttcggaact      300 ggaaccaagg tcaccgtcct a                                                321

<210> SEQ ID NO 19
<211> LENGTH: 107
<212> TYPE: PRT
<213> ORGANISM: Homo sapiens

<400> SEQUENCE: 19
```

Ser Tyr Glu Leu Thr Gln Pro Pro Ser Val Ser Val Ser Pro Gly Gln
1               5                   10                  15

Thr Ala Arg Ile Thr Cys Ser Gly Glu Ala Leu Pro Lys Gln Tyr Ala
            20                  25                  30

Ser Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Asn Gly Ala Tyr
                85                  90                  95

Val Phe Gly Thr Gly Thr Lys Val Thr Val Leu
            100                 105

<210> SEQ ID NO 20
<211> LENGTH: 318
<212> TYPE: DNA
<213> ORGANISM: Homo sapiens

<400> SEQUENCE: 20
tcctatgagc tgactcagcc actctcagtg tcagtggccc tgggacagac ggccaggatt      60
acctgtgggg gaaacaacat tggaagtaaa aatgtgcact ggtaccagca gaagccaggc     120
caggcccctg tgctggtcat ctatagggat agcaaccggc cctctgggat ccctgagcga     180
ttctctggct ccaactcggg gaacacggcc accctgacca tcagcagagc ccaagccggg     240
gatgaggctg actattactg tcaggtgtgg gacagcagca ctgcggtatt cggcggaggg     300
accaagctga ccgtccta                                                   318

<210> SEQ ID NO 21
<211> LENGTH: 106
<212> TYPE: PRT
<213> ORGANISM: Homo sapiens

<400> SEQUENCE: 21

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala Val
                85                  90                  95

Phe Gly Gly Gly Thr Lys Leu Thr Val Leu
            100                 105

<210> SEQ ID NO 22
<211> LENGTH: 366
<212> TYPE: DNA
<213> ORGANISM: Homo sapiens

<400> SEQUENCE: 22
caggtgcaac tggtgcagtc tggggctgag gtgaagaagc ctggggcctc agtgaaggtc      60

```
tcctgcaagg cttctggata caccttcacc ggctactttt ttcactgggt gcgacaggcc    120
cctggacaag ggcttgagtg ggtgggatgg atcaaccctc acagtggtgc cacacacttt    180
gcacagaaat ttcagggcag ggtcaccatg accagggaca cgtccatcag tacagcctac    240
atggaactga gcaggctgag atctgacgac acggccgtgt attactgtgc gagagatggc    300
tccaactgga accgcgacta cggtatggac gtctggggcc aggggaccac ggtcaccgtc    360
tcctca                                                              366
```

\<210\> SEQ ID NO 23
\<211\> LENGTH: 122
\<212\> TYPE: PRT
\<213\> ORGANISM: Homo sapiens

\<400\> SEQUENCE: 23

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Phe Phe His Trp Val Arg Gln Ala Pro Gly Gln Gly Leu Glu Trp Val
        35                  40                  45

Gly Trp Ile Asn Pro Asn Ser Gly Ala Thr His Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Ser Asn Trp Asn Arg Asp Tyr Gly Met Asp Val Trp
            100                 105                 110

Gly Gln Gly Thr Thr Val Thr Val Ser Ser
        115                 120
```

\<210\> SEQ ID NO 24
\<211\> LENGTH: 330
\<212\> TYPE: DNA
\<213\> ORGANISM: Homo sapiens

\<400\> SEQUENCE: 24

```
cagtctgtgc tgactcagcc accctcagcg tctgggaccc ccgggcagag ggtcaccatc     60
tcttgttctg gaagcagctc caacatcgga attaatcatg tatattggta ccagcaactc    120
ccaggaacgg cccccaaaat cttcatctat aggaataatc agcggccctc aggggtccct    180
gaccgattct ctggctccaa gtctggcacc tcagcctccc tggccatcag tgggctccgg    240
tccgaggatg aggctgatta ttactgtgca gtatgggatg acagtctgag tggtgtggta    300
ttcggcggag ggaccaagct gaccgtccta                                     330
```

\<210\> SEQ ID NO 25
\<211\> LENGTH: 111
\<212\> TYPE: PRT
\<213\> ORGANISM: Homo sapiens

\<400\> SEQUENCE: 25

```
Gln Ser Val Leu Thr Gln Pro Pro Ser Ala Ser Gly Thr Pro Gly Gln
1               5                  10                  15

Arg Val Thr Ile Ser Cys Ser Gly Ser Ser Ser Asn Ile Gly Ile Asn
            20                  25                  30

His Val Tyr Trp Tyr Gln Gln Leu Pro Gly Thr Ala Pro Lys Ile Phe
```

```
                35                  40                  45
Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Val Trp Asp Asp Ser Leu
                 85                  90                  95

Ser Gly Val Val Phe Gly Gly Gly Thr Lys Leu Thr Val Leu Gly
            100                 105                 110

<210> SEQ ID NO 26
<211> LENGTH: 363
<212> TYPE: DNA
<213> ORGANISM: Homo sapiens

<400> SEQUENCE: 26
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg gctggagtg gtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatctg     300
ggagcagcag ctggtactgg ttttgactac tggggccagg gaaccctggt caccgtctcc     360
tca                                                                    363

<210> SEQ ID NO 27
<211> LENGTH: 121
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Gly Ala Ala Ala Gly Thr Gly Phe Asp Tyr Trp Gly
            100                 105                 110

Gln Gly Thr Leu Val Thr Val Ser Ser
        115                 120

<210> SEQ ID NO 28
<211> LENGTH: 333
<212> TYPE: DNA
<213> ORGANISM: Homo sapiens

<400> SEQUENCE: 28
cagtctgtgt tgacgcagcc gccctcagtg tctgcggccc caggacagaa ggtcaccatc      60
tcctgctctg gaagcagctc caacattggg aataattatg tatcctggta ccagcagctc     120
```

```
ccaggaacag ccccccaaact cctcatttat gacaataata agcgaccctc agggattcct      180
gaccgattct ctggctccaa gtctggcacg tcagccaccc tgggcatcac cggactccag      240
actggggacg aggccgatta ttactgcgga acatgggata gcagcctgag tgctggtgtg      300
gtattcggcg gagggaccaa gctgaccgtc cta                                   333
```

<210> SEQ ID NO 29
<211> LENGTH: 111
<212> TYPE: PRT
<213> ORGANISM: Homo sapiens

<400> SEQUENCE: 29

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Val Phe Gly Gly Gly Thr Lys Leu Thr Val Leu
            100                 105                 110

<210> SEQ ID NO 30
<211> LENGTH: 375
<212> TYPE: DNA
<213> ORGANISM: Homo sapiens

<400> SEQUENCE: 30

```
caggtacagc tgcagcagtc aggtccagga ctggtgaagc cctcgcagac cctctcactc      60
acctgtgcca tctccgggga cagtgtctct agcaacagag ctgcttggaa ctggatcagg      120
cagtccccat cgagaggcct tgagtggctg ggaaggacat actacaggtc caagtggtat      180
aatgattttg cagtatctgt gagaagtcga ataaccatca ccccagacac atccaagaac      240
cagttctccc tgcagctgaa ctctgtgact cccgaggaca cggctgtgta ttactgtgca      300
agagatagga acagtggcta ctactactac ggtttggacg tctggggcca agggaccacg      360
gtcaccgtct cctca                                                      375
```

<210> SEQ ID NO 31
<211> LENGTH: 125
<212> TYPE: PRT
<213> ORGANISM: Homo sapiens

<400> SEQUENCE: 31

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Phe Ala
    50                  55                  60

Val Ser Val Arg Ser Arg Ile Thr Ile Thr Pro Asp Thr Ser Lys Asn

```
            65                  70                  75                  80
Gln Phe Ser Leu Gln Leu Asn Ser Val Thr Pro Glu Asp Thr Ala Val
                    85                  90                  95

Tyr Tyr Cys Ala Arg Asp Arg Asn Ser Gly Tyr Tyr Tyr Gly Leu
                100                 105                 110

Asp Val Trp Gly Gln Gly Thr Thr Val Thr Val Ser Ser
            115                 120                 125

<210> SEQ ID NO 32
<211> LENGTH: 321
<212> TYPE: DNA
<213> ORGANISM: Homo sapiens

<400> SEQUENCE: 32
aaaatagtga tgacgcagtc tccagctacc ctgtctgtgt ctccagggga aagagccacc      60
ctctcctgca gggccagtca gagtgttagt aacaacttag cctggtatca gcagaaacct     120
ggccaggctc ccaggctcct catctatggt gcatccacca gggccactgg tatcccagcc     180
aggttcagtg gcagtgggtc tgggacagag ttcactctca ccatcaccag cctacagtct     240
gaagattttg cagtttatta ctgtcagcag tataataact ggcctctcac tttcggcgga     300
gggaccaagg tggagatcaa a                                                321

<210> SEQ ID NO 33
<211> LENGTH: 107
<212> TYPE: PRT
<213> ORGANISM: Homo sapiens

<400> SEQUENCE: 33

Lys Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 34
<211> LENGTH: 375
<212> TYPE: DNA
<213> ORGANISM: Homo sapiens

<400> SEQUENCE: 34
caggtacagc tgcagcagtc aggtccagga ctggtgaagc cctcgcagac cctctcactc      60
acctgtgcca tctccgggga cagtgtctct agcaacagag ctgcttggaa ctggatcagg     120
cagtccccat cgagaggcct tgagtggctg gaaggacat actacaggtc caagtggtat      180
aatgatcatg cagtatctgt gaaaagtcga ataaccatca ccccagacac atccaagaac     240
cagttctccc tgcagctgaa ctctgtgact cccgaggaca agctgtgta ttactgtgca      300 agagatagga acagtggcta ctactactac ggtttggacg tctggggcca agggaccacg     360
```
gtcaccgtct cctca                                                      375

<210> SEQ ID NO 35
<211> LENGTH: 125
<212> TYPE: PRT
<213> ORGANISM: Homo sapiens

<400> SEQUENCE: 35

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp His Ala
    50                  55                  60

Val Ser Val Lys Ser Arg Ile Thr Ile Thr Pro Asp Thr Ser Lys Asn
65                  70                  75                  80

Gln Phe Ser Leu Gln Leu Asn Ser Val Thr Pro Glu Asp Lys Ala Val
                85                  90                  95

Tyr Tyr Cys Ala Arg Asp Arg Asn Ser Gly Tyr Tyr Tyr Gly Leu
            100                 105                 110

Asp Val Trp Gly Gln Gly Thr Thr Val Thr Val Ser Ser
        115                 120                 125

<210> SEQ ID NO 36
<211> LENGTH: 321
<212> TYPE: DNA
<213> ORGANISM: Homo sapiens

<400> SEQUENCE: 36
gaaatagtga tgacgcagtc tccagccacc ctgtctgtgt ctccagggga aagagccacc     60
ctctcctgca gggccagtca gagtgttagt aacaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcaccag cctacagtct   240
gaagattttg cagtttatta ctgtcagcag tataataact ggcctctcac tttcggcgga   300
gggaccaagg tggagatcaa a                                             321

<210> SEQ ID NO 37
<211> LENGTH: 107
<212> TYPE: PRT
<213> ORGANISM: Homo sapiens

<400> SEQUENCE: 37

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Leu
                85                  90                  95

```
Thr Phe Gly Gly Gly Thr Lys Val Glu Ile Lys
            100                 105

<210> SEQ ID NO 38
<211> LENGTH: 473
<212> TYPE: PRT
<213> ORGANISM: Artificial sequence
<220> FEATURE:
<223> OTHER INFORMATION: 1A1 human-mouse chimera

<400> SEQUENCE: 38

Met Asp Met Arg Val Pro Ala Gln Leu Leu Gly Leu Leu Leu Leu Trp
1               5                   10                  15

Leu Arg Gly Ala Arg Cys Glu Val Gln Leu Val Gln Ser Gly Ala Glu
                20                  25                  30

Val Lys Lys Pro Gly Glu Ser Leu Lys Ile Ser Cys Lys Gly Ser Gly
            35                  40                  45

Tyr Asn Phe Ile Ser His Trp Ile Gly Trp Val Arg Gln Met Pro Gly
50                  55                  60

Lys Gly Leu Glu Trp Met Gly Met Ile Tyr Pro Gly Asp Ser Asp Thr
65                  70                  75                  80

Arg Tyr Ser Pro Ser Phe Gln Gly Gln Val Thr Ile Ser Ala Asp Lys
                85                  90                  95

Ser Ile Asn Thr Ala Tyr Leu Gln Trp Arg Ser Leu Lys Ala Ser Asp
            100                 105                 110

Thr Ala Met Tyr Phe Cys Ala Arg His Gly Gly Ile Thr Gly Thr Thr
        115                 120                 125

Phe Tyr Tyr Asp Phe Gly Met Asp Val Trp Gly Gln Gly Thr Thr Val
130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
210                 215                 220

Gly Thr Gln Thr Tyr Thr Cys Asn Val Asp His Lys Pro Ser Asn Thr
225                 230                 235                 240

Lys Val Asp Lys Thr Val Pro Arg Asp Cys Gly Cys Lys Pro Cys
                245                 250                 255

Ile Cys Thr Val Pro Glu Val Ser Ser Val Phe Ile Phe Pro Pro Lys
            260                 265                 270

Pro Lys Asp Val Leu Thr Ile Thr Leu Thr Pro Lys Val Thr Cys Val
        275                 280                 285

Val Val Asp Ile Ser Lys Asp Asp Pro Glu Val Gln Phe Ser Trp Phe
290                 295                 300

Val Asp Asp Val Glu Val His Thr Ala Gln Thr Gln Pro Arg Glu Glu
305                 310                 315                 320

Gln Phe Asn Ser Thr Phe Arg Ser Val Ser Glu Leu Pro Ile Met His
                325                 330                 335

Gln Asp Trp Leu Asn Gly Lys Glu Phe Lys Cys Arg Val Asn Ser Ala
            340                 345                 350

Ala Phe Pro Ala Pro Ile Glu Lys Thr Ile Ser Lys Thr Lys Gly Arg
```

```
                        355                 360                 365
Pro Lys Ala Pro Gln Val Tyr Thr Ile Pro Pro Lys Glu Gln Met
370                 375                 380

Ala Lys Asp Lys Val Ser Leu Thr Cys Met Ile Thr Asp Phe Phe Pro
385                 390                 395                 400

Glu Asp Ile Thr Val Glu Trp Gln Trp Asn Gly Gln Pro Ala Glu Asn
                405                 410                 415

Tyr Lys Asn Thr Gln Pro Ile Met Asp Thr Asp Gly Ser Tyr Phe Val
                420                 425                 430

Tyr Ser Lys Leu Asn Val Gln Lys Ser Asn Trp Glu Ala Gly Asn Thr
                435                 440                 445

Phe Thr Cys Ser Val Leu His Glu Gly Leu His Asn His His Thr Glu
                450                 455                 460

Lys Ser Leu Ser His Ser Pro Gly Lys
465                 470

<210> SEQ ID NO 39
<211> LENGTH: 108
<212> TYPE: PRT
<213> ORGANISM: Artificial
<220> FEATURE:
<223> OTHER INFORMATION: Light chain consensus
<220> FEATURE:
<221> NAME/KEY: misc_feature
<222> LOCATION: (5)..(5)
<223> OTHER INFORMATION: Xaa can be Thr or Met
<220> FEATURE:
<221> NAME/KEY: misc_feature
<222> LOCATION: (25)..(25)
<223> OTHER INFORMATION: Xaa can be Glu or Asp
<220> FEATURE:
<221> NAME/KEY: misc_feature
<222> LOCATION: (33)..(33)
<223> OTHER INFORMATION: Xaa can be Ser or Tyr
<220> FEATURE:
<221> NAME/KEY: misc_feature
<222> LOCATION: (44)..(44)
<223> OTHER INFORMATION: Xaa can be Leu or Val
<220> FEATURE:
<221> NAME/KEY: misc_feature
<222> LOCATION: (49)..(49)
<223> OTHER INFORMATION: Xaa can be Arg or Lys
<220> FEATURE:
<221> NAME/KEY: misc_feature
<222> LOCATION: (51)..(51)
<223> OTHER INFORMATION: Xaa can be Thr or Ser
<220> FEATURE:
<221> NAME/KEY: misc_feature
<222> LOCATION: (57)..(57)
<223> OTHER INFORMATION: Xaa can be Ile or Leu
<220> FEATURE:
<221> NAME/KEY: misc_feature
<222> LOCATION: (93)..(93)
<223> OTHER INFORMATION: Xaa can be Asn or Gly
<220> FEATURE:
<221> NAME/KEY: misc_feature
<222> LOCATION: (95)..(95)
<223> OTHER INFORMATION: Xaa can be Ala or Ser
<220> FEATURE:
<221> NAME/KEY: misc_feature
<222> LOCATION: (96)..(96)
<223> OTHER INFORMATION: Xaa can be Tyr or none
<220> FEATURE:
<221> NAME/KEY: misc_feature
<222> LOCATION: (104)..(104)
<223> OTHER INFORMATION: Xaa can be Arg or Lys

<400> SEQUENCE: 39

Ser Tyr Glu Leu Xaa Gln Pro Pro Ser Val Ser Val Ser Pro Gly Gln
1               5                   10                  15
```

-continued

```
Thr Ala Arg Ile Thr Cys Ser Gly Xaa Ala Leu Pro Lys Gln Tyr Ala
            20                  25                  30

Xaa Trp Tyr Gln Gln Lys Pro Gly Gln Ala Pro Xaa Leu Val Ile Tyr
        35                  40                  45

Xaa Asp Xaa Glu Arg Pro Ser Gly Xaa Pro Glu Arg Phe Ser Gly Ser
 50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Xaa Gly Xaa Xaa
                85                  90                  95

Tyr Val Phe Gly Thr Gly Thr Xaa Val Thr Val Leu
            100                 105
```

<210> SEQ ID NO 40
<211> LENGTH: 126
<212> TYPE: PRT
<213> ORGANISM: Artificial
<220> FEATURE:
<223> OTHER INFORMATION: Heavy chain consensus
<220> FEATURE:
<221> NAME/KEY: misc_feature
<222> LOCATION: (14)..(14)
<223> OTHER INFORMATION: Xaa can be Pro or Ser
<220> FEATURE:
<221> NAME/KEY: misc_feature
<222> LOCATION: (28)..(28)
<223> OTHER INFORMATION: Xaa can be Ser or Asn
<220> FEATURE:
<221> NAME/KEY: misc_feature
<222> LOCATION: (30)..(30)
<223> OTHER INFORMATION: Xaa can be Ser or Ile or Thr
<220> FEATURE:
<221> NAME/KEY: misc_feature
<222> LOCATION: (31)..(31)
<223> OTHER INFORMATION: Xaa can be Asn or Ser
<220> FEATURE:
<221> NAME/KEY: misc_feature
<222> LOCATION: (32)..(32)
<223> OTHER INFORMATION: Xaa can be Tyr or His
<220> FEATURE:
<221> NAME/KEY: misc_feature
<222> LOCATION: (50)..(50)
<223> OTHER INFORMATION: Xaa can be Ile or Met
<220> FEATURE:
<221> NAME/KEY: misc_feature
<222> LOCATION: (77)..(77)
<223> OTHER INFORMATION: Xaa can be Arg or Asn
<220> FEATURE:
<221> NAME/KEY: misc_feature
<222> LOCATION: (84)..(84)
<223> OTHER INFORMATION: Xaa can be Ser or Arg
<220> FEATURE:
<221> NAME/KEY: misc_feature
<222> LOCATION: (95)..(95)
<223> OTHER INFORMATION: Xaa can be Tyr or Phe
<220> FEATURE:
<221> NAME/KEY: misc_feature
<222> LOCATION: (100)..(100)
<223> OTHER INFORMATION: Xaa can be Lys or Gly
<220> FEATURE:
<221> NAME/KEY: misc_feature
<222> LOCATION: (111)..(111)
<223> OTHER INFORMATION: Xaa can be Tyr or Phe

<400> SEQUENCE: 40

```
Glu Val Gln Leu Val Gln Ser Gly Ala Glu Val Lys Lys Xaa Gly Glu
1               5                   10                  15

Ser Leu Lys Ile Ser Cys Lys Gly Ser Gly Tyr Xaa Phe Xaa Xaa Xaa
            20                  25                  30

Trp Ile Gly Trp Val Arg Gln Met Pro Gly Lys Gly Leu Glu Trp Met
        35                  40                  45
```

Gly Xaa Ile Tyr Pro Gly Asp Ser Asp Thr Arg Tyr Ser Pro Ser Phe
          50                  55                  60

Gln Gly Gln Val Thr Ile Ser Ala Asp Lys Ser Ile Xaa Thr Ala Tyr
 65                  70                  75                  80

Leu Gln Trp Xaa Ser Leu Lys Ala Ser Asp Thr Ala Met Tyr Xaa Cys
              85                  90                  95

Ala Arg His Xaa Gly Ile Thr Gly Thr Thr Phe Tyr Tyr Asp Xaa Gly
             100                 105                 110

Met Asp Val Trp Gly Gln Gly Thr Thr Val Thr Val Ser Ser
         115                 120                 125

<210> SEQ ID NO 41
<211> LENGTH: 107
<212> TYPE: PRT
<213> ORGANISM: Artificial
<220> FEATURE:
<223> OTHER INFORMATION: Light chain consensus
<220> FEATURE:
<221> NAME/KEY: misc_feature
<222> LOCATION: (1)..(1)
<223> OTHER INFORMATION: Xaa can be Lys or Glu

<400> SEQUENCE: 41

Xaa Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Asn Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Thr Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 42
<211> LENGTH: 125
<212> TYPE: PRT
<213> ORGANISM: Artificial Sequence
<220> FEATURE:
<223> OTHER INFORMATION: Heavy chain consensus
<220> FEATURE:
<221> NAME/KEY: misc_feature
<222> LOCATION: (63)..(63)
<223> OTHER INFORMATION: Xaa can be Phe or His
<220> FEATURE:
<221> NAME/KEY: misc_feature
<222> LOCATION: (68)..(68)
<223> OTHER INFORMATION: Xaa can be Arg or Lys
<220> FEATURE:
<221> NAME/KEY: misc_feature
<222> LOCATION: (94)..(94)
<223> OTHER INFORMATION: Xaa can be Thr or Lys

<400> SEQUENCE: 42

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                 20                  25                  30

Arg Ala Ala Trp Asn Trp Ile Arg Gln Ser Pro Ser Arg Gly Leu Glu

```
                35                  40                  45
Trp Leu Gly Arg Thr Tyr Tyr Arg Ser Lys Trp Tyr Asn Asp Xaa Ala
 50                  55                  60

Val Ser Val Xaa Ser Arg Ile Thr Ile Thr Pro Asp Thr Ser Lys Asn
 65                  70                  75                  80

Gln Phe Ser Leu Gln Leu Asn Ser Val Thr Pro Glu Asp Xaa Ala Val
                 85                  90                  95

Tyr Tyr Cys Ala Arg Asp Arg Asn Ser Gly Tyr Tyr Tyr Gly Leu
                100                 105                 110

Asp Val Trp Gly Gln Gly Thr Thr Val Thr Val Ser Ser
            115                 120                 125

<210> SEQ ID NO 43
<211> LENGTH: 256
<212> TYPE: PRT
<213> ORGANISM: Artificial Sequence
<220> FEATURE:
<223> OTHER INFORMATION: Flag/Fc construct

<400> SEQUENCE: 43

Met Glu Thr Asp Thr Leu Leu Leu Trp Val Leu Leu Leu Trp Val Pro
 1               5                  10                  15

Gly Ser Thr Gly Asp Asp Tyr Lys Asp Asp Asp Lys Asp Lys Thr
                 20                  25                  30

His Thr Cys Pro Pro Cys Pro Ala Pro Glu Leu Leu Gly Gly Pro Ser
                 35                  40                  45

Val Phe Leu Phe Pro Pro Lys Pro Lys Asp Thr Leu Met Ile Ser Arg
 50                  55                  60

Thr Pro Glu Val Thr Cys Val Val Val Asp Val Ser His Glu Asp Pro
 65                  70                  75                  80

Glu Val Lys Phe Asn Trp Tyr Val Asp Gly Val Glu Val His Asn Ala
                 85                  90                  95

Lys Thr Lys Pro Arg Glu Glu Gln Tyr Asn Ser Thr Tyr Arg Val Val
                100                 105                 110

Ser Val Leu Thr Val Leu His Gln Asp Trp Leu Asn Gly Lys Glu Tyr
                115                 120                 125

Lys Cys Lys Val Ser Asn Lys Ala Leu Pro Ala Pro Ile Glu Lys Thr
            130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
                180                 185                 190

Asn Gly Gln Pro Glu Asn Asn Tyr Lys Thr Thr Pro Pro Val Leu Asp
                195                 200                 205

Ser Asp Gly Ser Phe Phe Leu Tyr Ser Lys Leu Thr Val Asp Lys Ser
            210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255
```